(12) United States Patent
Wong et al.

(10) Patent No.: US 6,462,193 B1
(45) Date of Patent: Oct. 8, 2002

(54) HYDROXYAZEPANES AS INHIBITORS OF GLYCOSIDASE AND HIV PROTEASE

(75) Inventors: Chi-Huey Wong, Rancho Santa Fe, CA (US); Francisco Moris-Varas, Chicago, IL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/367,919

(22) PCT Filed: Feb. 21, 1997

(86) PCT No.: PCT/US97/02927

§ 371 (c)(1),
(2), (4) Date: Aug. 23, 1999

(87) PCT Pub. No.: WO98/37218

PCT Pub. Date: Aug. 27, 1998

(51) Int. Cl.$^7$ ............................................. C07D 223/08
(52) U.S. Cl. ....................................................... 540/604
(58) Field of Search ......................................... 540/604

(56) References Cited

PUBLICATIONS

Paulsen, et al., "Synthese und Reaktionen von Keto–piperidinosen", *Chem. Ber. 100*: 802–815 (1967).

Withers, et al., "Identification of a Covalent α–D–Glucopyranosyl Enzyme Intermediate Formed on a β–Glucosidase", *J. Am. Chem. Soc.* 110:8551–8553 (1988).

Ganem, et al., "Mimicking the Glucosidase Transition State: Shape/Charge Considerations", *J. Am. Chem. Soc.* 113: 8984–8985 (1991).

Erickson, "Design and Structure of Symmetry–Based Inhibitors of HIV–1 Protease", *Perspect. Drug Dis. Design* 1: 109–128 (1993).

Papandreou, et al., "Amidine, Amidrazone, and Amidoxime Derivatives of Monosacchardie Aldonolactams: Synthesis and Evaluation as Glycosidase Inhibitors", *J. Am. Chem. Soc.* 115: 11682–11690 (1993).

Lam, et al., "Rational Design of Potent, Bioavailable, Nonpeptide Cyclic Ureas as HIV Protease Inhibitors", *Science* 263: 380–384 (1994).

Farr, et al., "Pyrrolidine and Hexahydro–1 H–Azepine Mimics of the 'Flap Up' Mannosyl Cation", *Tetrahedron* 50: 1033–1044 (1994).

Poitout, et al., "Polyhydroxylated Piperidines and Azepanes from D–Mannitol. Synthesis of 1–Deoxynojirimycin and Analogues", *Tet. Lett.* 35: 3293–3296 (1994).

Fotsch, et al., "Synthesis of a Guanidino–Sugar as a Glycosyl Cation Mimic", *Tet. Lett.* 35: 3481–3484 (1994).

Wong, et al., "Enzymes in Organic Synthesis: Application to the Problems of Carbohydrate Recognition (Part 1)", *Angew. Chem. Int. Ed. Engl.* 34: 412–432 (1995).

Wong, et al., "Enzymes in Organic Synthesis: Application to the Problems of Carbohydrate Recognition (Part 2)", *Angew Chem. Int. Ed. Engl.* 34: 521–546 (1995).

Alajarín, et al., "A Short, Enzymatic Synthesis of L–Glucose from Dihydroxyacetone Phosphate and L–Glyceraldehyde", *J. Org. Chem.* 60: 4294–4295 (1995).

Wong, et al., "Enzymatic Synthesis of L–Fucose and Analogs", *J. Org. Chem.* 60: 7360–7363 (1995).

Sham, et al., "A Novel, Picomolar Inhibitor of Human Immunodeficiency Virus Type 1 Protease", *J. Med. Chem.* 39: 392–397 (1996).

Page, et al., "An Improved Chemical and Enzymatic Synthesis of New Fructose Derivatives for Improt Studies by the Glucose Transporter in Parasites", *Tetrahedron* 52: 1557–1572 (1996).

Jadhav, et al., "Synthesis of 7–Membered Cyclic Oxamides: Novel HIV–1 Protease Inhibitors", *Tet. Lett.* 37: 1153–1156 (1996).

Jeong, et al., "Cyclic Guanidino–Sugars with Low p$K_a$ as Transition–State Analog Inhibitors of Glycosidases: Neutral Instead of Charged Species Are the Active Forms", *J. Am. Chem. Soc.* 118: 4227–4234 (1996).

Moris–Varas et al., Enzymatic/Chemical Synthesis and Biological Evaluation of Seven–Membered Iminocyclitols, Journal of the American Chemical Society, vol. 118, No. 33, pp. 7647–7652, Aug. 1996.*

Qian et al., Synthesis of C.sub.2–Symmetrical Polyhydroxyazepanes as Inhibiotrs of Glycosidases, Bioorganic and Medicinal Chemistry Letters, vol. 6, No. 10, pp. 1117–1122, 1996.*

Lohray et al., Umprecedented Selectivity in the Reaction of 1,2:5,6–Dianhydro–3,4–O–Isopropylidenehexitols with Benzylamine: A Practical Synthesis of 3,4,5,6–Tetrahydroxyazepanes, Journal of Organic Chemistry, vol. 60, No. 18, pp. 5958–5960, Sep. 1995.*

* cited by examiner

*Primary Examiner*—Brenda Coleman
(74) *Attorney, Agent, or Firm*—Donald G. Lewis

(57) ABSTRACT

Hydroxyazepanes display inhibitory activity with respect to glycosidase, with $K_i$ values from-moderate to low micromolar range. Benzyl and 3,6-dibenzyl derivatives of hydroxyazepanes display inhibitory activity with respect to HIV protease. These compounds are synthesized either by chemoenzymatic or chemical methodologies.

7 Claims, 20 Drawing Sheets

| # | [I] μM | α-Mannosidase from jack beans | α-Galactosidase from green coffee beans | β-Galactosidase from Aspergillus niger | α-Glucosidase from yeast | β-Glucosidase from sweet almonds | β-N-Acetyl-glucosaminidase from jack beans | α-Fucosidase from bovine kidney |
|---|---|---|---|---|---|---|---|---|
| 1 | 120 | 31 (187 ± 26) | 87 (5.4 ± 0.56) | 9 | 13 | 16 | NI | 95 (4.6 ± 0.7) |
| 2 | 160 | 18 | 25 (216 ± 19) | 49 (50 ± 4) | NI | 14 | 35 | 57 |
| 3 | 240 | NI | NI | NI | 21 | NI | 94 (4.6 ± 0.4) | 16 |
| 4 | 240 | 30 (364 ± 49) | NI | 15 | 15 | 13 | 22 | 89 (10.6 ± 0.7) |
| 5 | 224 | 14 | NI | NI | NI | 14 | 41 (269 ± 20) | 42 |
| 6[a] | 200 | 81 (25.7 ± 1.3) | 65 (67 ± 4.5) | 95 (6.5 ± 1.2) | 78 (29.4 ± 2.2) | 92 (12.8 ± 0.7) | 89 (22.7 ± 2.6) | 44 |
| 7[a] | 160 | 11 | NI | NI | 6 | 14 | 6 | 88 (23.4 ± 3.8) |
| 8[a] | 200 | 48 | 31 | 3 | NI | 78 (30.5 ± 2.5) | NI | 5 |

| Bond lengths [Å], (standard deviation ± 10⁻³ Å) | | | |
|---|---|---|---|
| O(1) - C(9) | 1.432 (4) | O(2) - C(10) | 1.438 (4) |
| O(3) - C(11) | 1.423 (5) | O(4) - C(12) | 1.441 (4) |
| N(1) - C(7) | 1.474 (5) | N(1) - C(13) | 1.479 (5) |
| N(1) - C(8) | 1.484 (5) | C(1) - C(6) | 1.377 (7) |
| C(1) - C(2) | 1.386 (8) | C(2) - C(3) | 1.385 (9) |
| C(3) - C(4) | 1.358 (10) | C(4) - C(5) | 1.388 (7) |
| C(5) - C(6) | 1.379 (6) | C(6) - C(7) | 1.511 (6) |
| C(8) - C(9) | 1.534 (6) | C(9) - C(10) | 1.516 (6) |
| C(10) - C(11) | 1.536 (5) | C(11) - C(12) | 1.507 (6) |
| C(12) - C(13) | 1.531 (6) | | |

| Bond angles [°], (standard deviation, ± 10⁻¹ °) | | | |
|---|---|---|---|
| C(7) - N(1) - C(13) | 108.0 (3) | C(7) - N(1) - C(8) | 112.9 (3) |
| C(13) - N(1) - C(8) | 114.1 (3) | C(6) - C(1) - C(2) | 120.8 (5) |
| C(3) - C(2) - C(1) | 119.4 (6) | C(4) - C(3) - C(2) | 120.4 (5) |
| C(3) - C(4) - C(5) | 119.9 (5) | C(6) - C(5) - C(4) | 120.8 (5) |
| C(1) - C(6) - C(5) | 118.7 (4) | C(1) - C(6) - C(7) | 120.9 (4) |
| C(5) - C(6) - C(7) | 120.4 (5) | N(1) - C(7) - C(6) | 113.1 (3) |
| N(1) - C(8) - C(9) | 117.7 (3) | O(1) - C(9) - C(10) | 109.8 (3) |
| O(1) - C(9) - C(8) | 109.4 (3) | C(10) - C(9) - C(8) | 112.6 (3) |
| O(2) - C(10) - C(9) | 108.0 (3) | O(2) - C(10) - C(11) | 109.7 (3) |
| C(9) - C(10) - C(11) | 114.5 (3) | O(3) - C(11) - C(12) | 108.0 (3) |
| O(3) - C(11) - C(10) | 109.6 (3) | C(12) - C(11) - C(10) | 115.9 (3) |
| O(4) - C(12) - C(11) | 109.9 (3) | O(4) - C(12) - C(13) | 109.3 (3) |
| C(11) - C(12) - C(13) | 114.6 (3) | N(1) - C(13) - C(12) | 114.1 (3) |

FIG. 10

| Compound and Essay Concentration | IC$_{50}$ (μM) | |
| --- | --- | --- |
| | HIV protease | FIV protease |
| 60a (80 μM, 40 μM, 20 μM) | 570 | 1400 |
| 60b (330 μM, 165 μM, 82 μM) | 380 | 670 |
| 64a (250 μM, 125 μM, 62 μM) | 675 | NI[b] |
| 64b (250 μM, 125 μM, 62 μM) | 1425 | NI[b] |
| 65a (160 μM, 80 μM, 40 μM) | 384 | weak inhibition[a] |
| 65b (260 μM, 130 μM, 65 μM) | 360 | NI[b] |

[a] weak inhibition stands for IC$_{50}$ > 1.5 mM. [b] stands for no inhibition.

FIG. 20

HYDROXYAZEPANES AS INHIBITORS OF GLYCOSIDASE AND HIV PROTEASE

CROSS-REFERENCE TO RELATED APPLICATION

The present application is a national stage entry under 35 U.S.C. §371 of PCT/US97/02927, filed Feb. 21, 1997.

This invention was made with government support under contract No. GM 44154 by the National Institutes of Health. The government has certain rights in the invention.

DESCRIPTION

Technical Field

The present invention relates to compounds that inhibit glycosidases and HIV proteases. More particularly, the present invention relates to seven-membered hydroxyiminocyclitols, also known as hydroxyazepanes, which have inhibitory activity toward glycosidases and hiv protease and to chemical and enzymatic/chemical methods for synthesizing such compounds.

BACKGROUND

Glycosidases are involved in the processing and synthesis of complex carbohydrates which are essential for various biological recognition processes. Because of their multifaceted biological importance, these enzymes are often targeted for inhibition. (Look et al. *Acc. Chem. Res.* 1993, 26, 182; Winchester et al. *Glycobiology* 1992, 2, 1991; Wong et al. *Angew. Chem. Int. Ed. Engl.* 1995, 34, 521; Legler et al. *Adv. Carbohydr. Chem. Biochem.* 1990, 48, 319; Sinnott et al. *Chem. Rev.* 1990, 90, 1171; Kirby et al. *Adv. Phys. Org. Chem.* 1994, 29, 87; Jacob et al. *Curr. Opin. Struct. Biol.* 1995, 5, 605.

Glycosidases and aspartyl proteases share a common mechanism in catalysis, i.e. both utilize two carboxyl groups as general acid and general base in the hydrolytic reactions (Wlodawer et al. *Science* 1989, 245, 616; Hyland et al. *Biochemistry* 1991, 30, 8454; Reviews on the mechanisms of glycosidases: Sinnott et al. *Chem. Rev.* 1990, 90, 1171; Legler et al. *Adv. Carb. Chem. Biochem.* 1990, 48, 319; Withers et al. *Pure & Appl. Chem.* 1995, 67, 1673).

Five- and six-membered azasugar families have been characterized as mimics of the transition state of the enzymatic reactions of glycosidases and aspartyl proteases. (Withers et al. *J. Am. Chem. Soc.* 1988, 110, 8551; Ganem et al. *J. Am. Chem. Soc.* 1991, 113, 8984; Papandreou et al. *J. Am. Chem. Soc.* 1993, 115, 11682; Fotsch et al. *Tetrahedron Lett.* 1994, 35, 3481; Jeong et al. *J. Am. Chem. Soc.*, 1996, 118, 4227.) Five- and six-membered iminocyclitols, for example, have been used as transition-state analog inhibitors of glycosidases (Elbein et al. *Annu. Rev. Biochem.* 1987, 56, 497; Wichester et al. *Glycobiology* 1992, 2, 199; Look et al. *Acc. Chem. Res.* 1993, 26, 182; Jacob et al. *Current Opinion in Structural Biology* 1995, 5, 605) and various peptide isosteres, including those with $C_2$-symmetry, have been developed as inhibitors of the HIV (Human Immunodeficiency Virus) protease (Erickson et al. *Perspectives in Drug Discovery and Design* 1993, 1, 109.)

Unlike five and six-membered iminocyclitols, the biological activities of seven-membered iminocyclitols, also known as hydroxyazepanes, are largely uncharacterized. One hydroxyazepane was reported to have no inhibitory activity against α-mannosidase. (Farr et al. *Tetrahedron* 1994, 50, 1033.) These heterocycles are conformationally more flexible than the corresponding six- and five-membered counterparts and may adopt the half-chair or pseudo-chair structure to mimic the transition state of the enzymatic glycosidic cleavage. (Qian et al. *Bioorg. Med. Chem. Lett.* 1996, 6, 1117.)

Conventional synthetic methods for producing hydroxyazepanes require lengthy linear chemical routes with multiple steps in overall low yields. (Paulsen et al. *Chem. Ber* 1967, 100, 512; Poitout et al. *Tetrahedron Lett.* 1994, 35, 3293; Lohray et al. *J. Org. Chem.* 1995, 60, 5958; Farr et al. *Tetrahedron* 1994, 50, 1033.)

What is needed is hydroxyazepanes having inhibitory activity with respect to glycosidases and aspartyl proteases and chemical or chemo/enzymatic methods for synthesizing hydroxyazepanes in high yields with a small number of synthetic steps.

SUMMARY OF THE INVENTION

One aspect of the invention is directed to methodologies for the chemical or chemo/enzymatic synthesis of seven-membered iminocyclitols which are also known as hydroxyazepanes. A series of hydroxyazepanes is obtained either by chemoenzymatic or chemical synthesis. The compounds display significant activity as glycosidase inhibitors, with $K_i$ values from moderate to low micromolar range. The 3-benzyl and 3,6-dibenzyl derivatives of these hydroxyazepanes, viz. compounds 60a, 60b, 64a, 64b, 65a, and 65b (FIGS. 8 and 20), inhibit the mechanistically related HIV protease.

In a first mode, a chemo/enzymatic methodology is employed for synthesizing hydroxyazepanes. In the first step, there is an addition of (±)-3-azido-2-hydroxypropanaldehyde with dihydroxyacetone phosphate (DHAP) in the presence of a DHAP dependent aldolase to produce a 6-azido-3,4,5-trihydroxy-2-hexanone-1-phosphate intermediate. In the second step, there is an hydrolysis of the 6-azido-3,4,5-trihydroxy-2-hexanone-1-phosphate intermediate to produce a polyhydroxy 6-deoxy-6-azido ketose by treatment with acid phosphatase. In the third step, there is an isomerization of the ketose to a 6-azido-6-deoxyaldopyranose by treatment with an isomerase. The fourth and final step comprises cyclization of the pyranose to a seven membered hydroxyazepane using reductive amination conditions on the C6 azide moiety of the pyranose with hydrogen and a catalyst.

Alternative modes include several novel chemical syntheses of hydroxyazepanes which involve chemical manipulations of aldopyranoses protected as benzyl glycosides or diisopropylidene ethers. All of the chemical syntheses involve the use of a Pd-mediated reductive amination conditions for ring expansion of the six membered pyranose to form the seven membered azepane. Examples of this chemical approach show that D-galactose can be used to obtain a meso-3,4,5,6-tetrahydroxyperhydroazepine; D-mannose can be used to obtain a derivative with a $C_2$ symmetry axis and N-acetylglucosamine can be used to obtain a 6-acetamidoiminocyclitol.

More particularly, one mode of the invention is directed to a method for producing a tetrahydroxyazepane. In this mode, there is an initial addition reaction of 3-azido-2-hydroxypropanaldehyde with dihydroxyacetone phosphate using an aldolase for producing a 6-azido-3,4,5-trihydroxy-2-hexanone-1-phosphate intermediate with the formula:

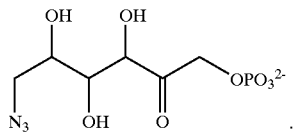

Then the above 6-azido-3,4,5-trihydroxy-2-hexanone-1-phosphate intermediate is hydrolyzed with acid phosphatase for producing a polyhydroxy 6-deoxy-6-azido ketose intermediate with the formula:

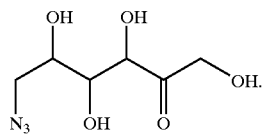

Then the above polyhydroxy 6-deoxy-6-azido ketose intermediate is isomerized with an isomerase for producing a 6-azido-6-deoxyaldose intermediate with the formula:

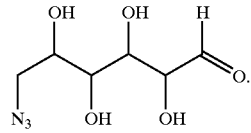

Then the above 6-azido-6-deoxyaldose intermediate is cyclized using reductive amination conditions with hydrogen and a catalyst for producing the tetrahydroxyazepane with the formula:

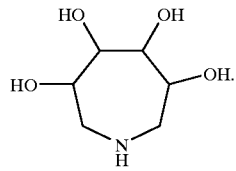

An alternative mode of the invention is directed to another method for synthesizing a tetrahydroxyazepane. The 6-hydroxyl position of a 6-hydroxy-1,2,3,4-protected monosaccharide is activated with an activating agent for producing an activated 6-hydroxy-1,2,3,4-protected monosaccharide with the formula:

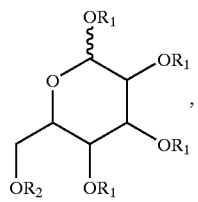

wherein $R_1$ is selected from the group consisting of benzyl and isopropylidene; $R_2$ is selected from the group consisting of tosylate and $(P(Phenyl)_3)^+$. Then the above activated 6-hydroxy-1,2,3,4-protected monosaccharide is admixed with an azide donor for producing a 6-azido-6-deoxy-1,2,3,4-protected monosaccharide with the formula:

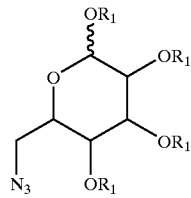

wherein $R_1$ is selected from the group consisting of benzyl and isopropylidene. Then, the above protected 6-azido-6-deoxy-1,2,3,4-protected monosaccharide is deprotected with a deprotecting agent for producing a 6-azido-6-deoxysugar with the formula:

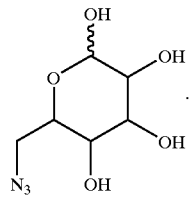

Then, the above 6-membered ring of the 6-azido-6-deoxysugar is expanded under reductive amination conditions with hydrogen and a catalyst for producing the tetrahydroxyazepane with the formula:

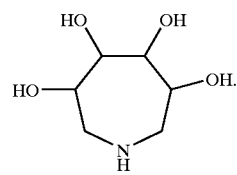

In a preferred mode, the 6-azido-6-deoxysugar is then converted into a 3-methoxy-tri-hydroxyazepane with additional steps. The 6-azido-6-deoxysugar is glycosylated with a glycosylating agent for producing a 6-azido-6-deoxyglycoside with the formula:

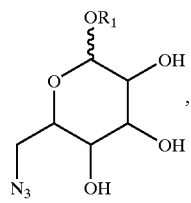

wherein $R_1$ is selected from the group consisting of methyl, propyl and benzyl. Then, the 3 and 4 hydroxyl positions on the above 6-azido-6-deoxyglycoside is blocked with a protecting agent for producing a 1,3,4,6-blocked 2-hydroxy-6-azido-6-deoxyglycoside with the formula:

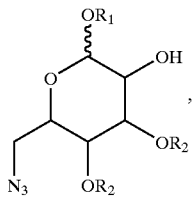

wherein $R_1$ is selected from the group consisting of isopropylidene and benzylidene. Then, the 2 hydroxyl position on the above 1,3,4,6-blocked 2-hydroxy-6-azido-6-deoxyglycoside is methylated with a methylating agent for producing a 1,3,4,6-blocked 2-methoxy-6-azido-6-deoxyglycoside with the formula:

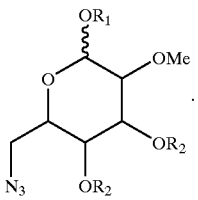

Then, the above 1,3,4,6-blocked 2-methoxy-6-azido-6-deoxyglycoside is deprotected with a deprotecting agent for producing a 2-methoxy-6-azido-6-deoxyglycoside with the formula:

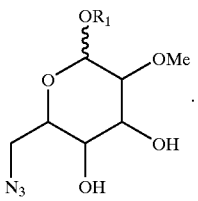

Then, the 6-membered ring of the above 2-methoxy-6-azido-6-deoxyglycoside is expanded using reductive amination conditions with hydrogen and a catalyst for producing the tetrahydroxyazepane with the formula:

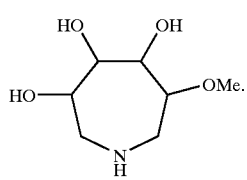

In an alternative mode of the invention, a 2-acetamido-3,4,5-trihydroxyazepane is synthesized by another method. The 6-hydroxyl position on a 2-acetamido-pyranose monosaccharide is activated with an activating agent for producing an activated 2-acetamido-pyranose monosaccharide with the formula:

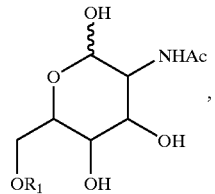

wherein $R_1$ is selected from the group consisting of tosylate and $(P(Phenyl)_3)^+$. Then, the above activated 2-acetamido-pyranose monosaccharide is admixed with an azide donor for producing a 6-azido-2-acetamido-pyranose monosaccharide with the formula:

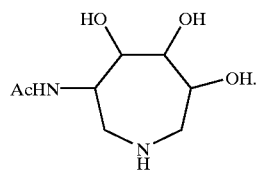

Then, the 6-membered ring of the above 6-azido-2-acetamido-pyranose monosaccharide is expanded using reductive amination conditions with hydrogen and a catalyst for producing the 2-acetamido-3,4,5-trihydroxyazepane with the formula:

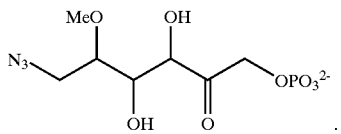

In an alternative mode of the invention, a 2-hydroxymethyl-3,4-dihydroxy-5-methoxypiperidine is synthesized by another method. In the first step, there is an addition of 3-azido-2-hydroxypropanaldehyde with dihydroxyacetone phosphate using an aldolase for producing a 6-azido-5-methoxy-3,4-dihydroxy-2-hexanone-1-phosphate intermediate with the formula:

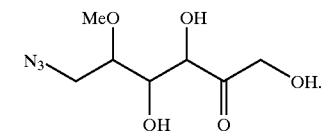

Then, the above 6-azido-5-methoxy-3,4-dihydroxy-2-hexanone-1-phosphate intermediate is dephosphorylated with acid phosphatase for producing a 6-azido-5-methoxy-1,3,4-trihydroxy-2-hexanone intermediate with the formula:

Then, the above 6-azido-5-methoxy-1,3,4-trihydroxy-2-hexanone intermediate is cyclized using reductive amination conditions with hydrogen and a catalyst for producing the 2-hydroxymethyl-3,4-dihydroxy-5-methoxypiperidine with the formula:

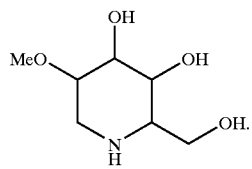

In each of the above alternative modes, the aldolase is selected from the group consisting of rhamnulose-1-phosphate aldolase, rabbit muscle aldolase, fructose-1,6-diphosphate aldolase and fucose aldolase. The isomerase is selected from the group consisting of rhamnose isomerase, fucose isomerase, glucose isomerase and galacatose isomerase. The catalyst is selected from the group consisting of palladium on carbon and platinum on carbon. The activating agent is selected from the group consisting of tosyl chloride and diethylazodicarboxylate with triphenylphosphine. The azide donor is selected from the group consisting of sodium azide and diphenylphosphorylazide. And, the deprotecting agent is selected from the group consisting of hydrogen with palladium on carbon, HCl/water combination and acetic acid/water combination.

In another aspect of the invention, tetrahydroxyazepane is synthesized according to the following method. A 6-azido-6-deoxyaldose intermediate with the formula:

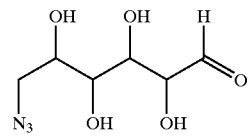

is cyclized using reductive amination conditions with hydrogen and a catalyst for producing the tetrahydroxyazepane with the formula:

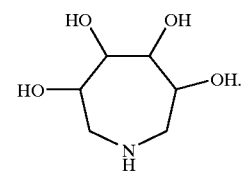

Another aspect of the invention is directed to active compounds represented by the following structures:

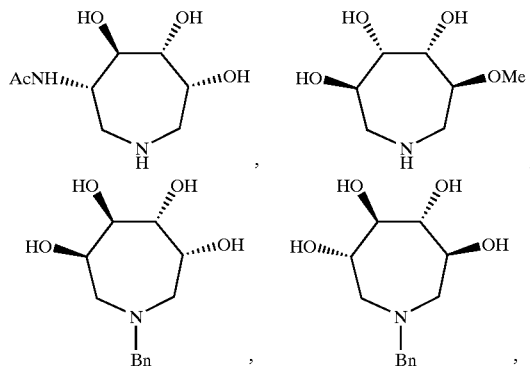

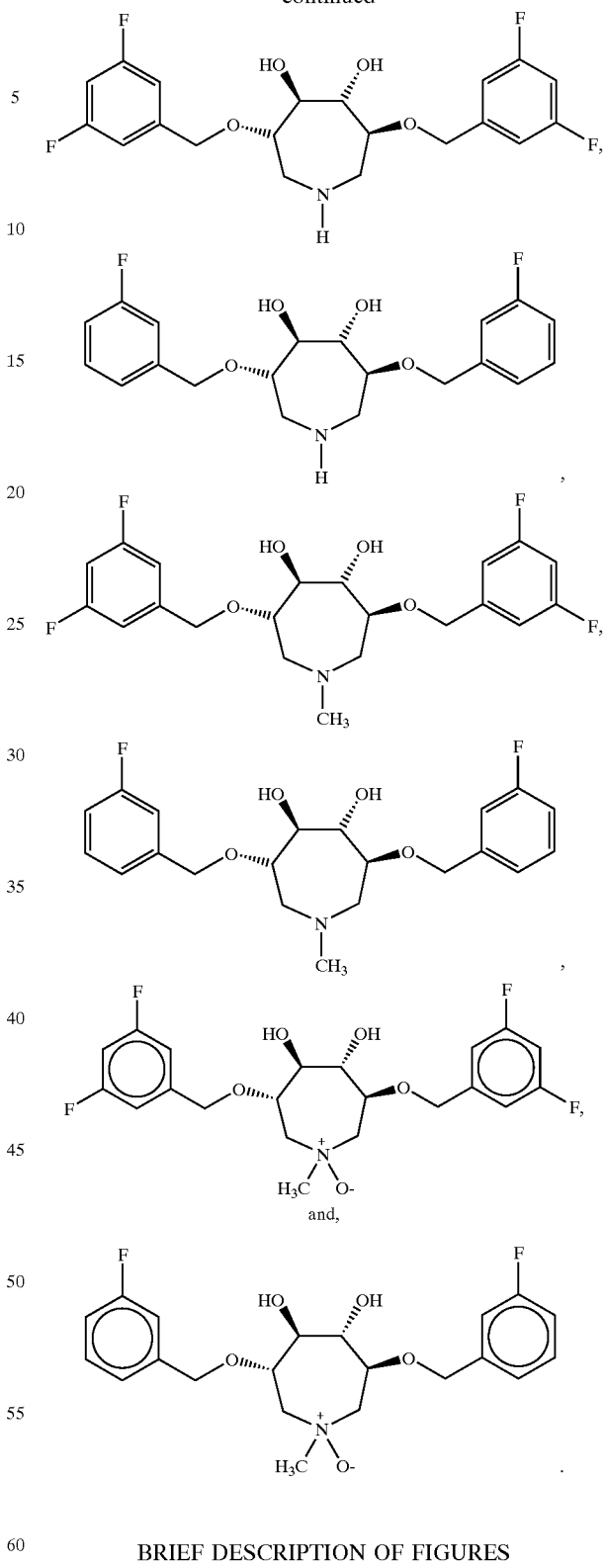

BRIEF DESCRIPTION OF FIGURES

FIG. 7 shows a table which highlights the inhibition of glycosidases with the seven-membered tetrahydroxy azepanes 1–8 wherein the percent inhibition at specified inhibitor concentration is provided in the first column; the preceding columns show competitive inhibition values and $K_i$ values ($\mu$M), which are given in parentheses; the letters NI indicate no inhibition; the sidenote "a" represents compounds prepared through epoxide opening according to the procedure described via Legler et al. *Adv. Carbohydr. Chem. Biochem.* 1990, 48, 319; Sinnott et al. *Chem. Rev.* 1990, 90, 1171; Kirby et al. *Adv. Phys. Org. Chem.* 1994, 29, 87; Jacob et al. *Curr. Opin. Struct. Biol.* 1995, 5, 605.

FIG. 10 shows the Bond lengths and angles for compound 7.

FIG. 12 illustrates the chemoenzymatic synthesis of tetrahydroxy azepanes 2 and 32.

FIG. 13 illustrates the chemoenzymatic synthesis of tetrahydroxy azepanes 1 and 3.

FIG. 14 illustrates the chemoenzymatic synthesis of tetrahydroxy azepanes 42 and 44.

FIG. 15 illustrates the chemoenzymatic synthesis of tetrahydroxy azepanes 37 and 39.

FIG. 20 shows data for the inhibition of HIV and FIV proteases with tetrahydroxy derivatives 60a, 60b, 64a, 64b, 65a, and 65b.

DETAILED DESCRIPTION OF THE INVENTION

Figure 1:
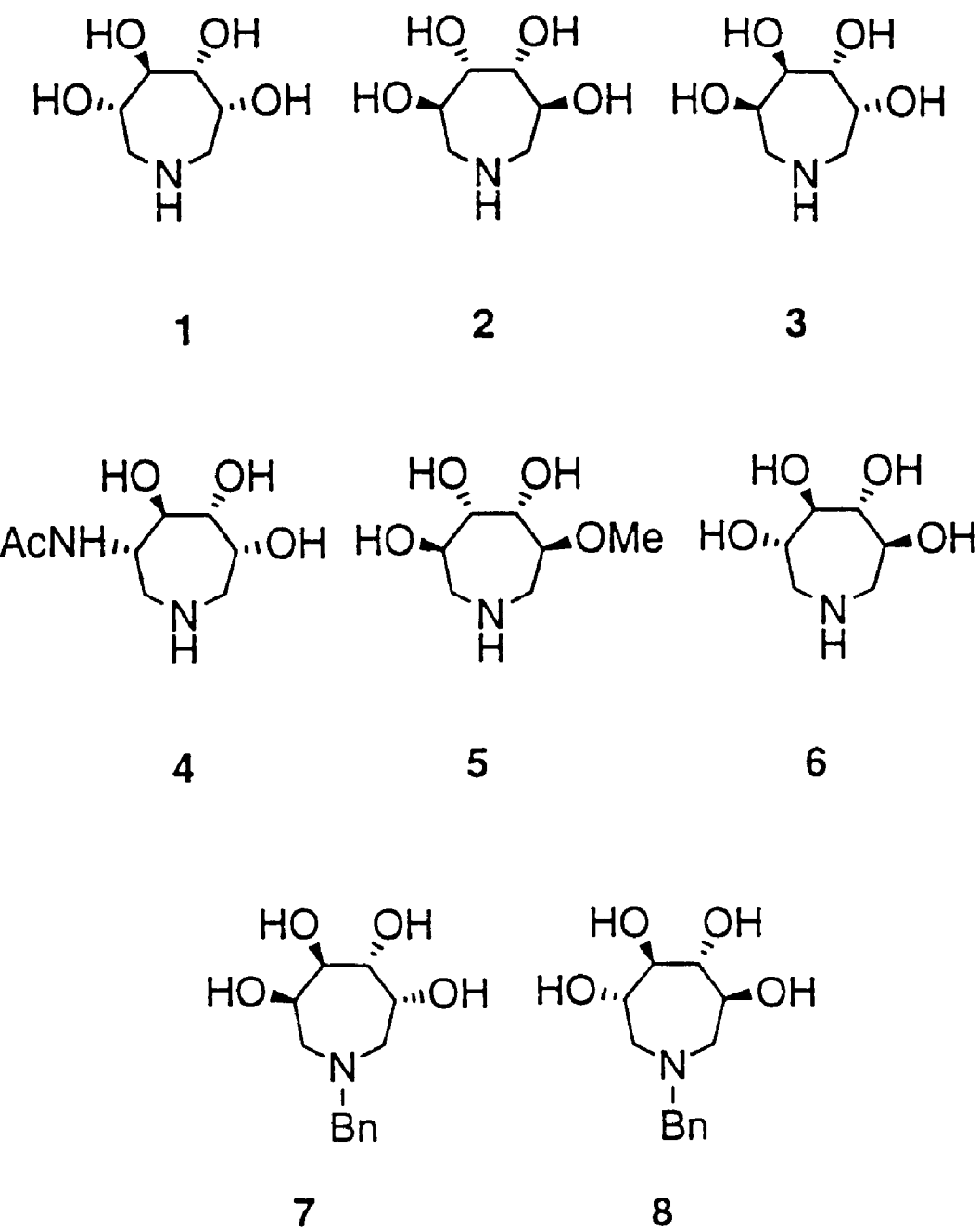
FIG. 1 illustrates the structures of eight tetrahydroxyazepanes with different stereoconfigurations about the 7-membered ring. Compounds 1–8 are synthesized via chemical or chemo/enzymatic routes.

The invention is directed to both chemical and chemo/enzymatic syntheses of seven-membered iminocyclitols which are also known as hydroxyazepanes. A series of hydroxyazepanes are obtained either by chemoenzymatic or chemical synthesis.

New efficient methods for the synthesis of 3,4,5,6-tetrahydroxyperhydroazepines (1–8) are claimed. Some of these seven-membered iminocyclitols are novel and some are inhibitors of glycosidases and HIV/FIV proteases. The seven-membered ring compounds are regarded to be conformationally more flexible than their five- and six-membered counterparts and hence may adopt a quasi-flattened conformation with minimum energetic demand, which could lead to a favorable binding in the enzyme active site. These heterocycles have been described in the literature (Paulsen et al. *Chem. Ber* 1967, 100, 512; Poitout et al. *Tetrahedron Lett.* 1994, 35, 3293; Lohray et al. *J. Org. Chem.* 1995, 60, 5958; Farr et al. *Tetrahedron* 1994, 50, 1033) but little is known regarding their biological activities, with the exception that one related compound was reported to have no inhibition activity against α-mannosidase (Lohray et al. *J. Org. Chem.* 1995, 60, 5958; Farr et al. *Tetrahedron* 1994, 50, 1033).

We find that many of these iminocyclitols are potent inhibitors of glycosidases and some even exhibit higher inhibition potencies than the five- and six-membered counterparts (FIG. 7).

As shown in FIG. 7, with each of the seven glycosidases investigated, there is at least one seven-membered iminocyclitol which exhibits potent inhibition of the enzyme with $K_i$ in the low $\mu$M range. Interestingly, compound 3 ($K_i$=4.6 $\mu$M) is better than 1-deoxy-N-acetylglucojirimycin ($K_i$=9.8 $\mu$M; Wong et al. *Angew. Chem. Int. Ed. Engl.* 1995, 34, 521) as inhibitor of β-N-acetylglucosaminidase, 6 ($K_i$=6.5 $\mu$M) is better than 1-deoxygalactojirimycin ($K_i>1$ mM; Bernotas et al. *Carbohydr. Res.* 1987, 167, 305 as inhibitor of β-galactosidase), and 6 ($K_i=25.7$ μM) is better than 1-deoxymannojirimycin ($K_i=150$ μM; Tulsiani et al. *J. Biol. Chem.* 1982, 257, 7936) as inhibitor of α-mannosidase. Compound 1 ($K_i=9.4$ μM) is, however, weaker than 1-deoxygalactojirimycin ($K_i=1.5$ nM) as inhibitor of α-galactosidase (Bernotas et al. *Carbohydr. Res.* 1987, 167, 305) and also weaker ($K_i=4.6$ μM) than 1-deoxyfucojirimycin ($K_i=5$ nM; Fleet et al. *J. Chem. Soc. Chem. Commun.* 1985, 841) as inhibitor of α-fucosidase. A similar situation was observed when compared to five-membered iminocyclitols (Wong et al. *Angew. Chem. Int. Ed. Engl.* 1995, 34, 521). It is also interesting that of these iminocyclitols examined, one of them with a $C_2$-symmetry (6) inhibits all glycosidases, including α-mannosidase. Benzylation of the nitrogen group of 3 and 6 (resulting in compounds 7 and 8) does not improve inhibition activity except in the case of α-fucosidase.

EXAMPLE 1

Chemo/enzymatic Synthesis of Azepanes

One embodiment of the invention comprises the chemo/enzymatic synthesis of hydroxyazepanes. The chemo/enzymatic synthesis of hydroxyazepanes (iminocyclitols) employs the combined use of aldolases and isomerases (FIG. 2) to form a 6-azido-6-deoxyaldose from acyclic precursors. From the 6-azido-6-deoxyaldose, the seven membered hydroxyazepane is then established in one step via a Pd-mediated ring cyclization using reductive amination conditions as described in the following example below.

Figure 2:
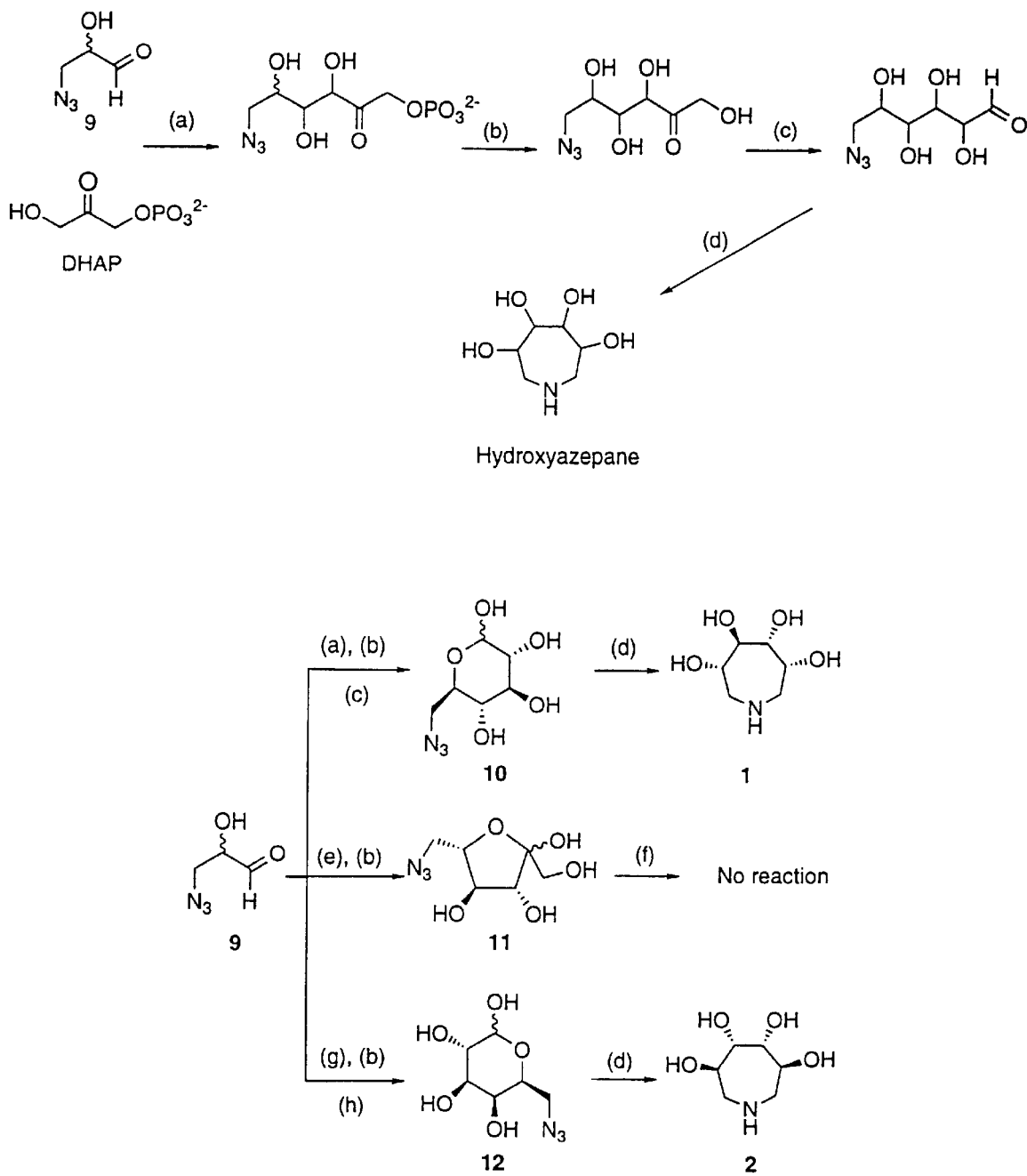
FIG. 2 is as follows: (1) the top scheme illustrates a general synthesis wherein step (a) addition of (±)-3-azido- 2-hydroxypropanaldehyde with dihydroxyacetone phosphate (DHAP) in the presence of a DHAP dependent aldolase to produce a 6-azido-3,4,5-trihydroxy-2-hexanone-1-phosphate intermediate. Step (b) comprises the hydrolysis of the 6-azido-3,4,5-trihydroxy-2-hexanone-1-phosphate intermediate to a polyhydroxy 6-deoxy-6-azido ketose by treatment with acid phosphatase. Step (c) comprises the isomerization of the ketose to a 6-azido-6-deoxyaldopyranose by treatment with an isomerase. Step (d) comprises cyclization of the pyranose to a seven membered hydroxyazepane using reductive amination conditions on the C6 azide moiety of the pyranose with hydrogen and a catalyst. (2) the lower scheme illustrates the synthesis of tetrahydroxy azepanes 1 and 2 wherein the indicated steps are as follows: (a) pH=6.7, DHAP (dihydroxyacetone phosphate), RAMA (rabbit muscle aldolase); (b) pH=4.5, Pase (acid phosphatase); (c) pH=7.2, TAKASWEET (GlcI-immobilized glucose isomerase, Miles Labs), 26% for 10 (d) $H_2$ (50 psi), Pd/C, $H_2O$, 2d, 91–94%; (e) pH=6.7, DHAP (dihydroxyacetone phosphate), RhaA (rhamnulose-1-phosphate aldolase); 30% for 11 (f) pH=7.2, RhaI (rhamnose isomerase); (g) pH=6.7, DHAP, FucA; (h) pH=7.2, FucI (fucose isomerase, 21%) for 12.

As a representative example of the chemo/enzymatic synthesis, illustrated in FIG. 2, (±)-3-azido-2-hydroxypropanaldehyde 9 and dihydroxyacetone phosphate (DHAP) are condensed in the presence of an aldolase, selected from the group consisting of fucose aldolase, tagatose aldolase, fructose 1,6-diphosphate aldolase and rhamnulose 1-phosphate aldolase, to form a 6-azido-3,4,5-trihydroxy-2-hexanone-1-phosphate intermediate which is followed by treatment with commercially available acid phosphatase (Pase) to cyclize the intermediate and form a 5-membered polyhydroxy 6-deoxy-6-azido ketose intermediate. This intermediate is then isomerase, selected from the group consisting of fucose isomerase, rhamnose isomerase and glucose isomerase, to provide a 6-membered 6-azido-6-deoxyaldopyranose which, after isolation, is exposed to ring expansion using reductive amination conditions (Paulsen et al. *Chem. Ber.* 1967, 100, 802) using hydrogen and Pd on carbon in water and affords the respective seven membered 3,4,5,6-tetrahdroxyazepane (Compounds 1 and 2).

Isomerization of the ketose to aldose for compounds 10 and 12 was performed with the use of glucose and fucose isomerases (GlcI and FucI), giving the equilibrium favoring aldose. Rhamnose isomerase (RhaI) was unable to isomerize azidoketose 11. It was found that in order for the seven membered ring to form, the ketose intermediate had to be converted into a aldose intermediate which was then cyclized to the seven membered ring. As an example, the case of compound 11 illustrates an attempt to prepare the seven-membered hydroxyazepane directly from an azido ketose catalyzed by reductive amination conditions. The procedure, however only produced the aminohexopyranose (Liu et al. *J Chem Soc Perkin Trans I* 1991, 1991, 2669) and under standard reductive amination conditions no reaction occurred.

In the final step, the intermediates 6-azido-6-deoxy-D-glucopyranose 10 and 6-azido-6-deoxy-L-galactopyranose 12 were subjected to Pd-mediated reductive amination conditions in aqueous solution in the presence of $H_2$ (50 psi) to give the seven membered (3R,4R,5R,6S)-tetrahydroxyperhydroazepine 1 and the meso iminocyclitol (3S,4R,5S,6R)-tetrahydroxyperhydroazepine 2 respectively (FIG. 2).

In the isomeration step, it was found that FucI prefers (2S,3R) and RhaI prefers the (2R,3R) aldose as substrate. Glucose isomerase prefers the (2R,3S) aldose as substrate. (For a review on the use of enzymes and specificities in chemical synthesis see Wong et al. *Enzymes in Synthetic Organic Chemistry*; Pergamon: Oxford, 1994. For synthethic work using isomerases see Fessner et al. *Tetrahedron Lett.* 1992, 33, 5231; Alajarin et al. *J. Org. Chem.* 1995, 60, 4294; Wong et al. *J. Org. Chem.* 1995, 60, 7360; Page et al. *Tetrahedron,* 1996, 52, 1557).

In an attempt to prepare 5 enzymatically (FIG. 6), (±)-3-azido-2-hydroxy-propanaldehyde dimethyl acetal was acetylated and kinetically resolved by lipase PS800 mediated hydrolysis (von der Osten et al. *J. Am. Chem. Soc.* 1989, 111, 3924). The products from this enzymatic reaction were methylated (MeI, NaH, THF) to give both enantiomers of 3-azido-2-O-methylpropanaldehyde diethyl acetal, 24 and 25, which were hydrolyzed and reacted with DHAP in the presence of fructose-1,6-diphosphate aldolase (FDPA) and rhamnulose-1-phosphate aldolase (RhaA) respectively. In both cases the methylated hydroxy aldehydes were substrates for the aldolases and (3S,4R,5R)-6-azido-5-methoxy-1,3,4-trihydroxyhexan-2-one, 26, and (3R,4S,5S)-6-azido-5-methoxy-1,3,4-trihydroxyhexan-2-one, 27 were obtained. These ketoses were, however, not accepted as substrates for GlcI and RhaI respectively. These observations are in agreement with the conclusion made by our group (Durrwachter et al. *J. Am. Chem. Soc.* 1986, 108, 7812) and others (Berger et al. *Tetrahedron Lett.* 1992, 33, 7125) that fructose analogues modified at carbon 5 (either inversion, deoxygenation or blocked hydroxyl) are not isomerized by GlcI. Similarly, (3R,4R,5S)-6-azido-5-methoxy-1,3,4-trihydroxyhexan-2-one was not accepted by FucI.

The ketoses 26 and 27 were then converted to (2R,3R,4S,5S)-2-hydroxymethyl-3,4-dihydroxy-5-methoxypiperidine (2-O-methyl-1-deoxymannojirimycin) 28 and the enantiomer 29 respectively under reductive amination conditions at 50 psi for 3 hours in MeOH. None of these two azasugars exhibited significant inhibition when tested for the glycosidases mentioned above.

EXAMPLE 2

Chemical Synthesis of Azepanes

Figure 3:
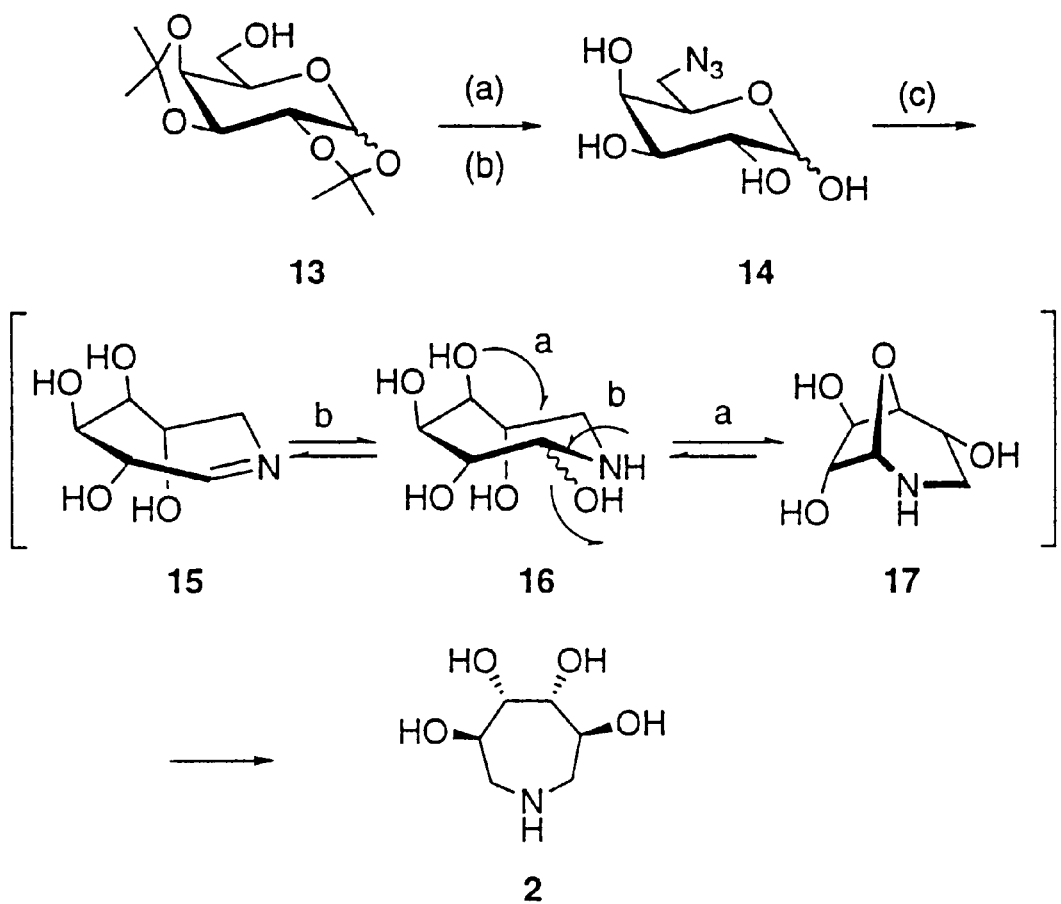
FIG. 3 illustrates the chemical synthesis of tetrahydroxyazepane 2 wherein the indicated steps are as follows: (a) (i) $Ph_3P$, DEAD (diethylazodicarboxylate), THF, 0° C.; (ii) $(PhO)_2P(O)N_3$ (diphenyl phosphoryl azide), 80%; (b) 80% AcOH, 70° C., 95%; (c) $H_2$ (50 psi), Pd/C, $H_2O$, 2d, 90%.

The chemical synthesis of hydroxyazepanes (iminocyclitols) starts with 6-azido-6-deoxysugars prepared from readily available protected monosaccharides (diisopropylidene sugars or benzyl pyranosides), the key step being again the reductive amination of a 6-azido-6-deoxyaldohexopyranose. Thus, 6-azido-6-deoxy-D-galactopyranose (14) (enantiomer of compound 12) undergoes ring expansion via Pd-mediated reductive amination in water to give 2 (FIG. 3). During the hydrogenation, compounds 2 and the intermediate 17 were observed by NMR in 12 hours. After 2 days, 17 disappeared and only 2 was obtained. It appears that 17 is formed via intramolecular dehydration of the intermediate 16 as illustrated in FIG. 3.

Figure 4:
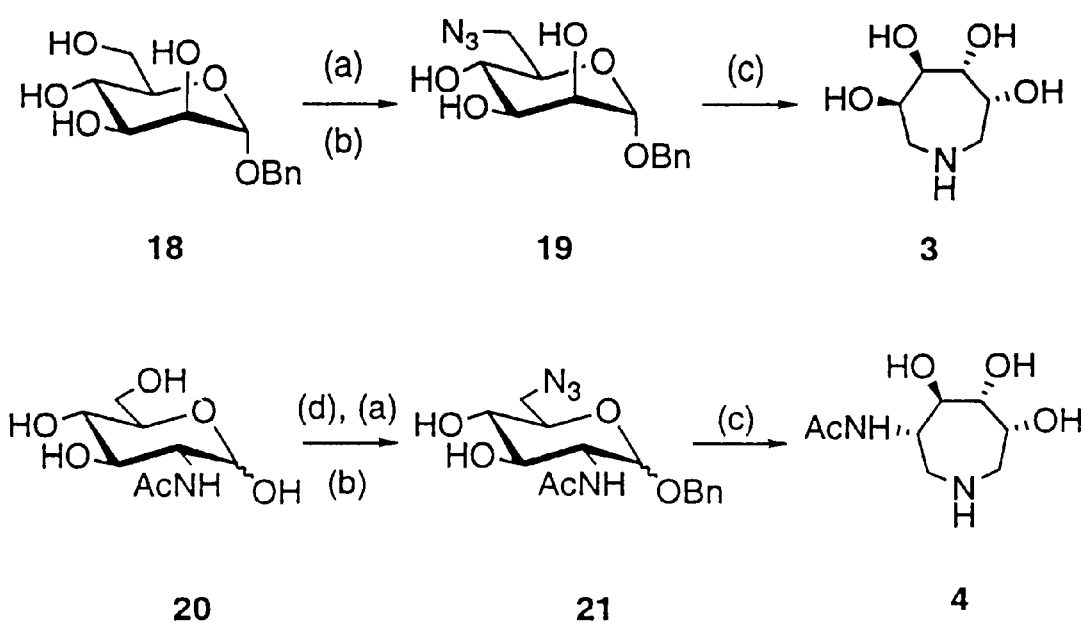
FIG. 4 illustrates the chemical synthesis of tetrahydroxyazepane 4 wherein the indicated steps are as follows: (a) TsCl (tosyl chloride), Py, 0° C., 12 h, 61–68%; (b) $NaN_3$ (5 eq), $NH_4Cl$, (5 eq), $EtOH:H_2O$ 9:1, reflux, 12 h, 70%; (c) $H_2$ (1 atm), Pd/C, $H_2O$, 12 h, 85%; (d) BnOH (benzyl alcohol), HCl, 80° C., 30%.

Benzyl pyranosides are easily prepared from aldopyranoses and represent a convenient entry-point to these seven-membered ring heterocycles. We illustrate this approach by using benzyl mannopyranoside and benzyl N-Acetylglucosamine as starting materials (FIG. 4). This approach is much more convenient than the bisepoxide opening described in the prior art (Legler et al. *Adv. Carbohydr. Chem. Biochem.* 1990, 48, 319; Sinnott et al. *Chem. Rev.* 1990, 90, 1171; Kirby et al. *Adv. Phys. Org. Chem.* 1994, 29, 87; Jacob et al. *Curr. Opin. Struct. Biol.* 1995, 5, 605), since mixtures of six and seven-membered rings are completely avoided. Tosylation of the primary hydroxyl group of 18 and benzyl pyranoside of 20 followed by azide displacement afford the azides 19 and 21. Hydrogenolysis of both compounds afforded the desired iminocyclitols, 3 and 4.

Figure 5:
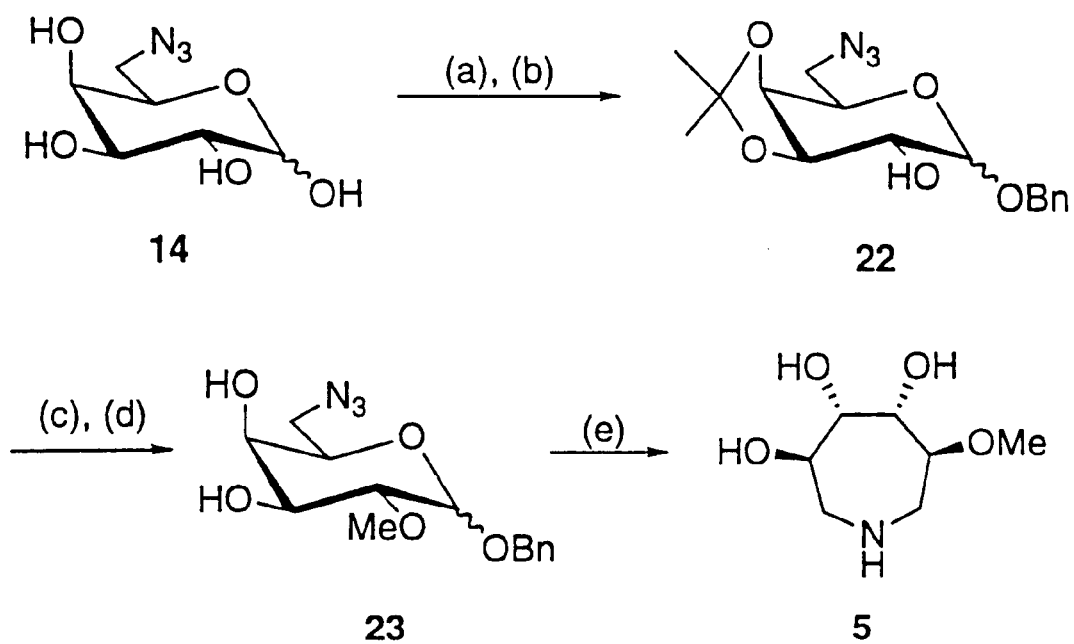
FIG. 5 illustrates the chemical synthesis of tetrahydroxyazepane 5 wherein the indicated steps are as follows: (a) BnOH, 80° C., $Et_2O \cdot BF_3$, 75%; (b) 2,2-dimethoxypropane, p-TSA, DMF, room temperature, 95%; (c) MeI, NaH, THF, room temperature, 93%; (d) 80% AcOH, 80° C., 95%; (e) $H_2$ (50 psi), Pd/C, $H_2O$, 2d, 90%.

The meso-iminocyclitol 2 was asymmetrized to (3S,4R, 5S,6R)-3-methoxy-4,5,6-trihydroxyazepine (5) from 6-azido-6-deoxy-D-galactopyranoside 14 via benzyl glycosilation, isopropylidene protection, methylation and reductive amination of the 2-O-methyl glycoside (23) as shown in FIG. 5.

Figure 9:
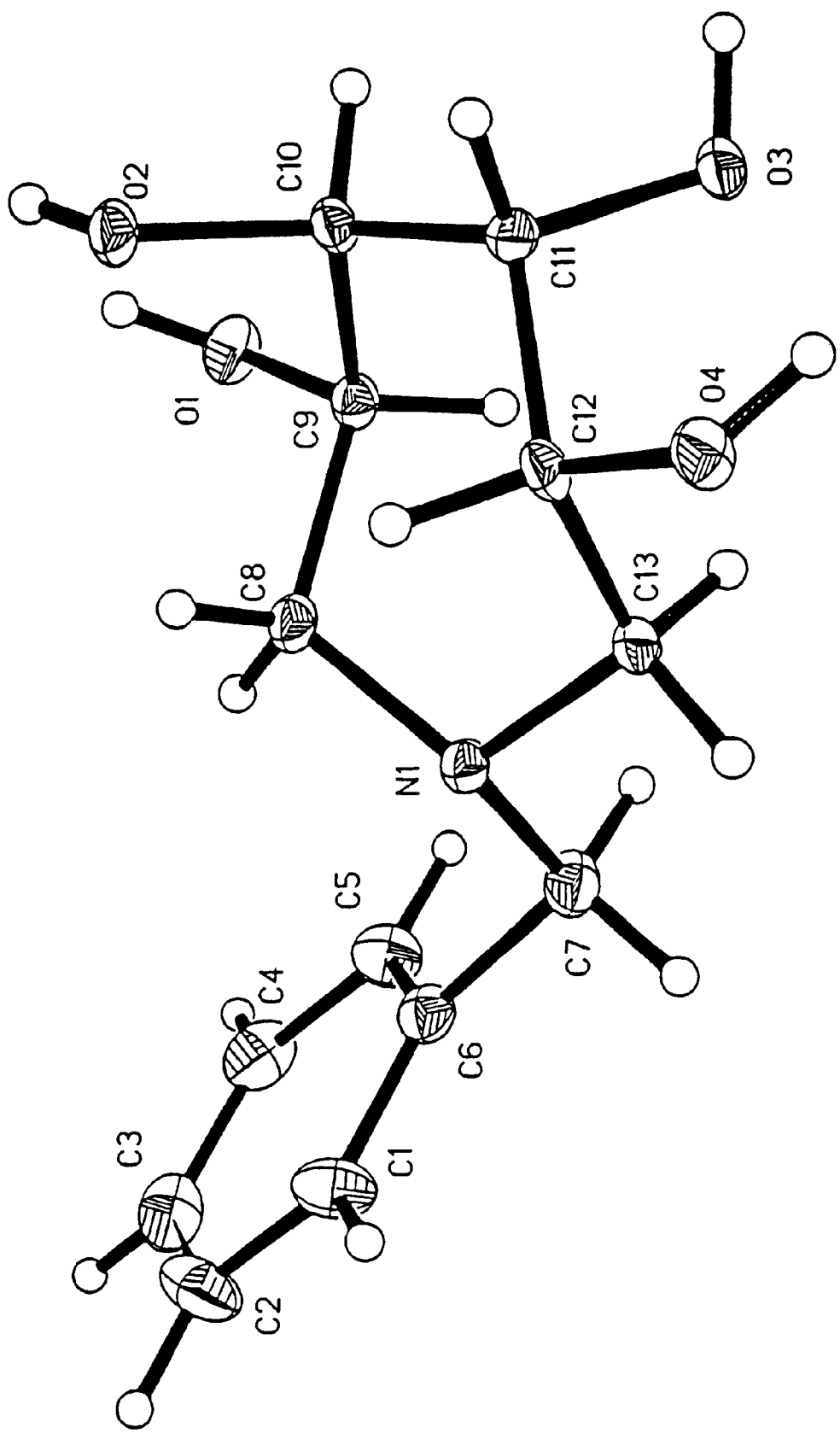
FIG. 9 illustrates an Ortep drawing of the X-ray crystal of a representative compound 7 which is shown to adopt a pseudo-chair conformation.
Figure 11:
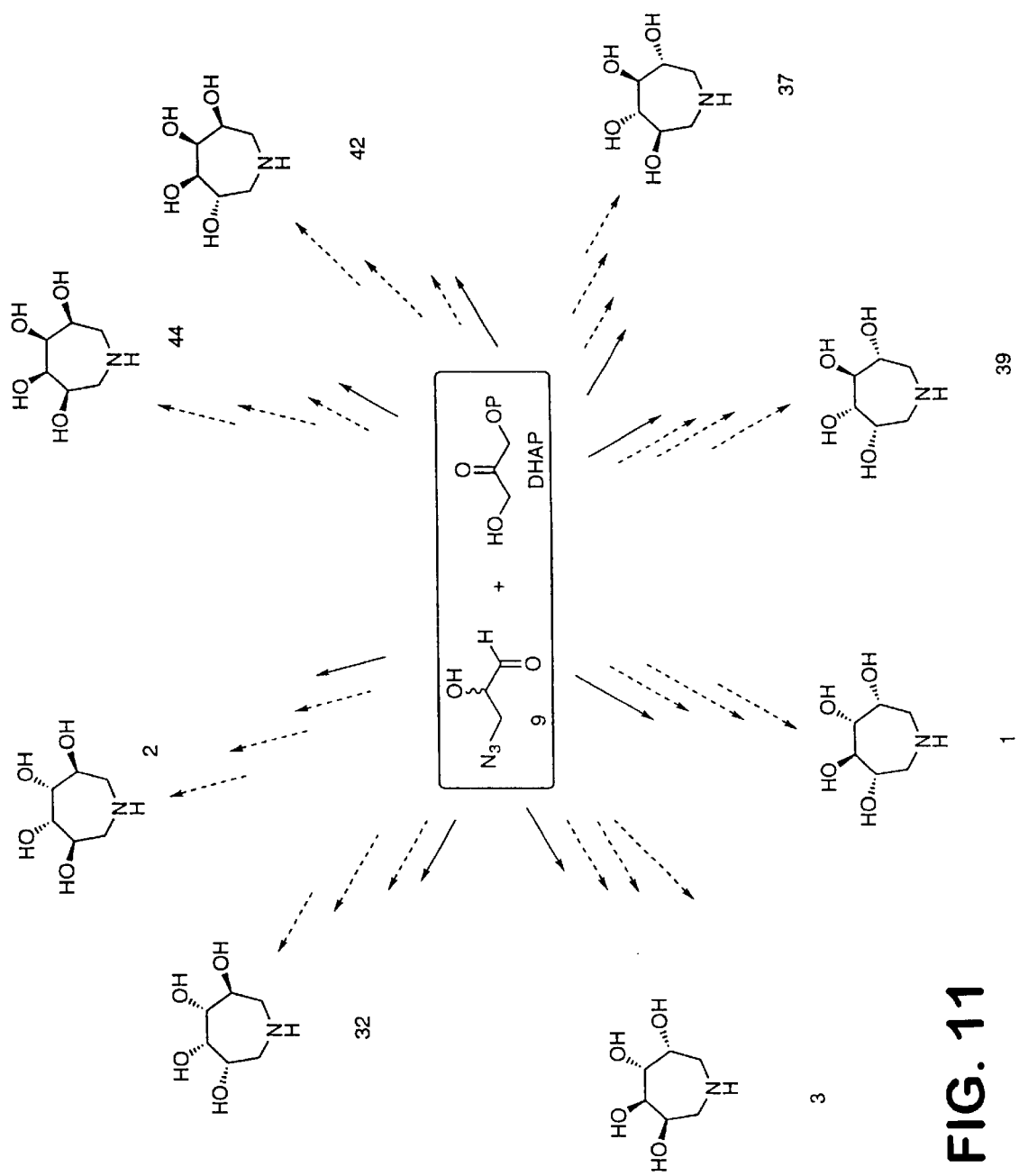
FIG. 11 illustrates various tetrahydroxy azepanes which can be obtained using a 4 step chemo/enzymatic methodology using various aldolases and isomerases to establish the desired stereochemistry.
Figure 12:
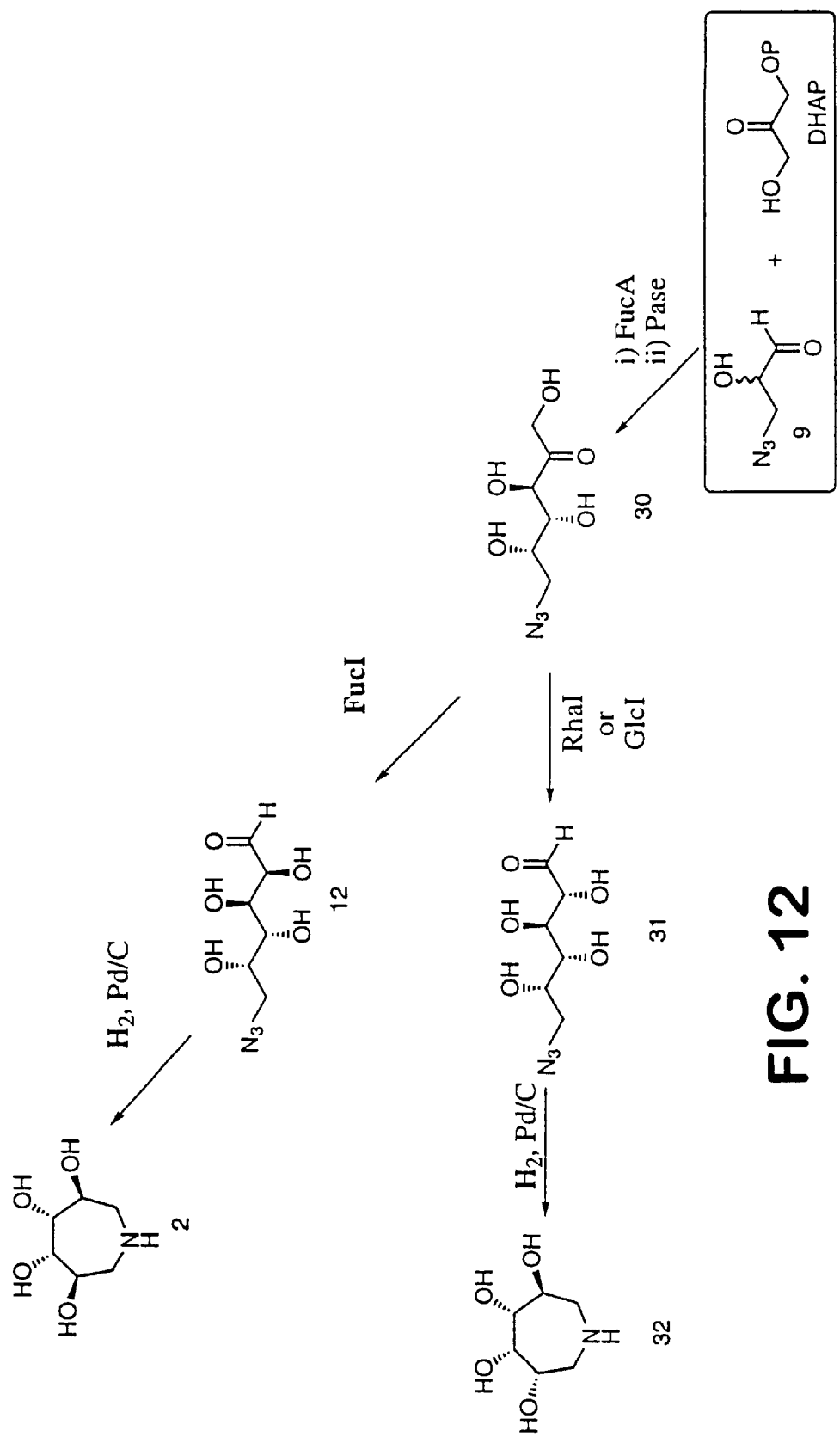
FIGS. 12–15 further elucidate the synthesis of the shown compounds.
Figure 13:
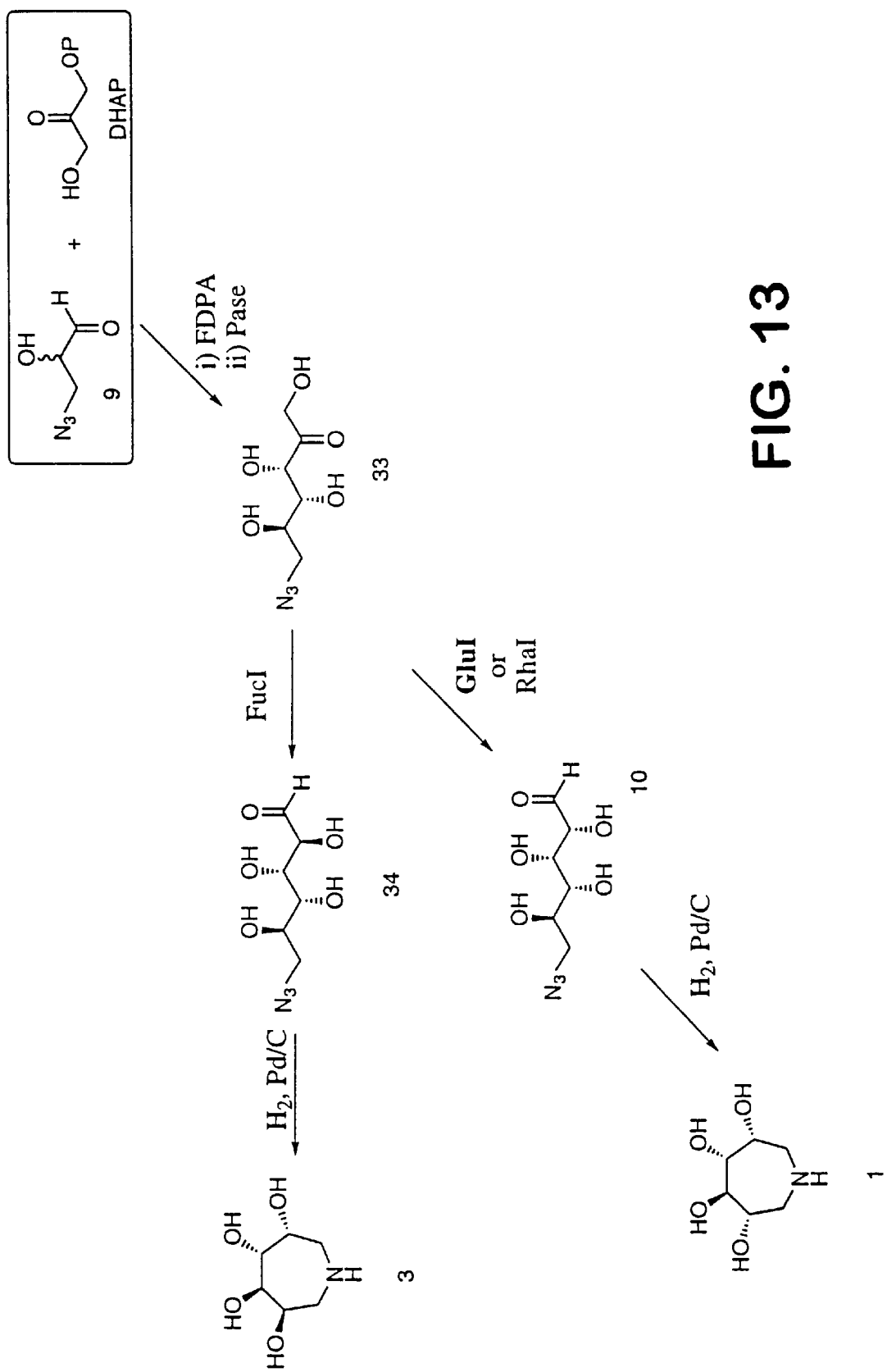
Figure 14:
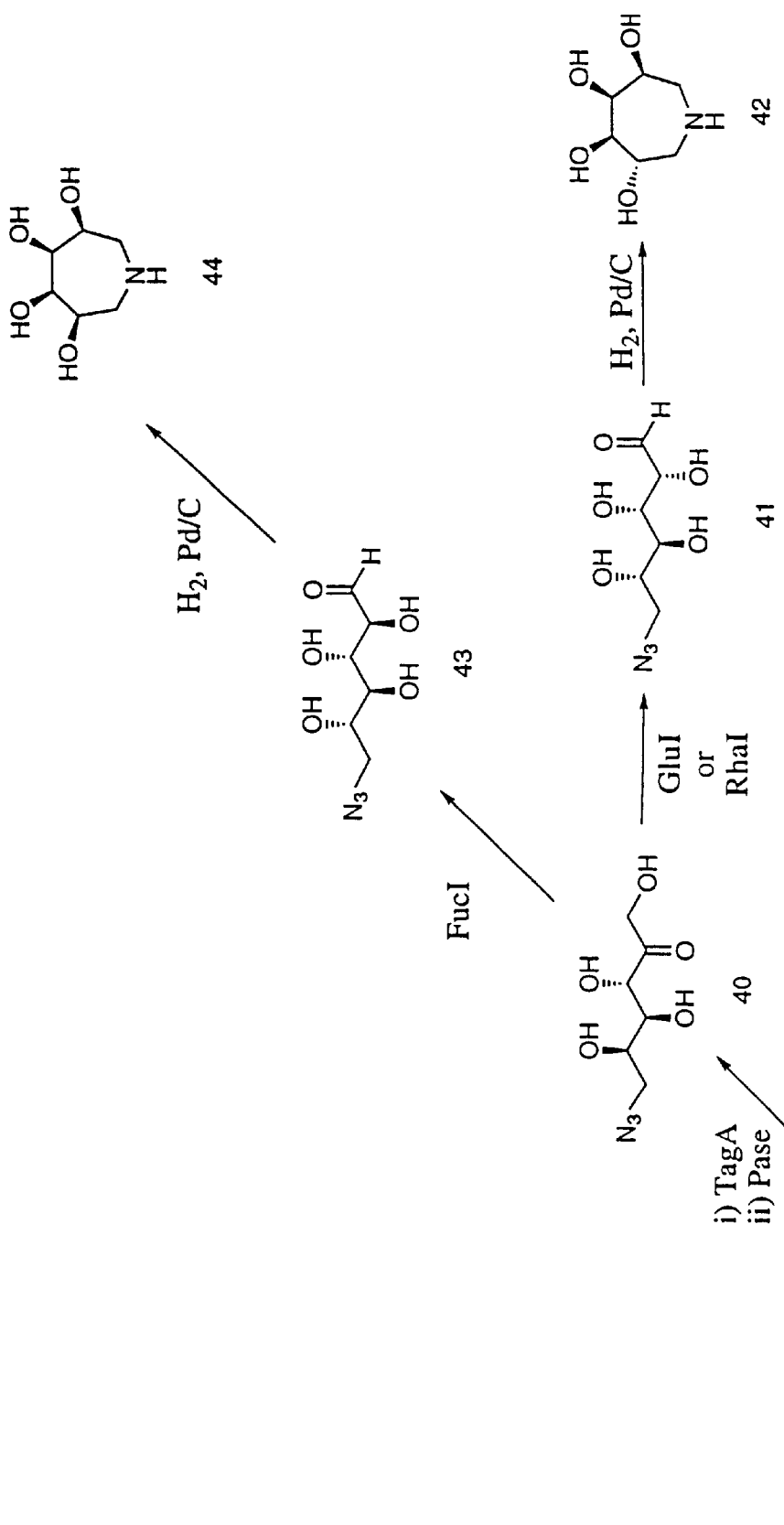
Figure 15:
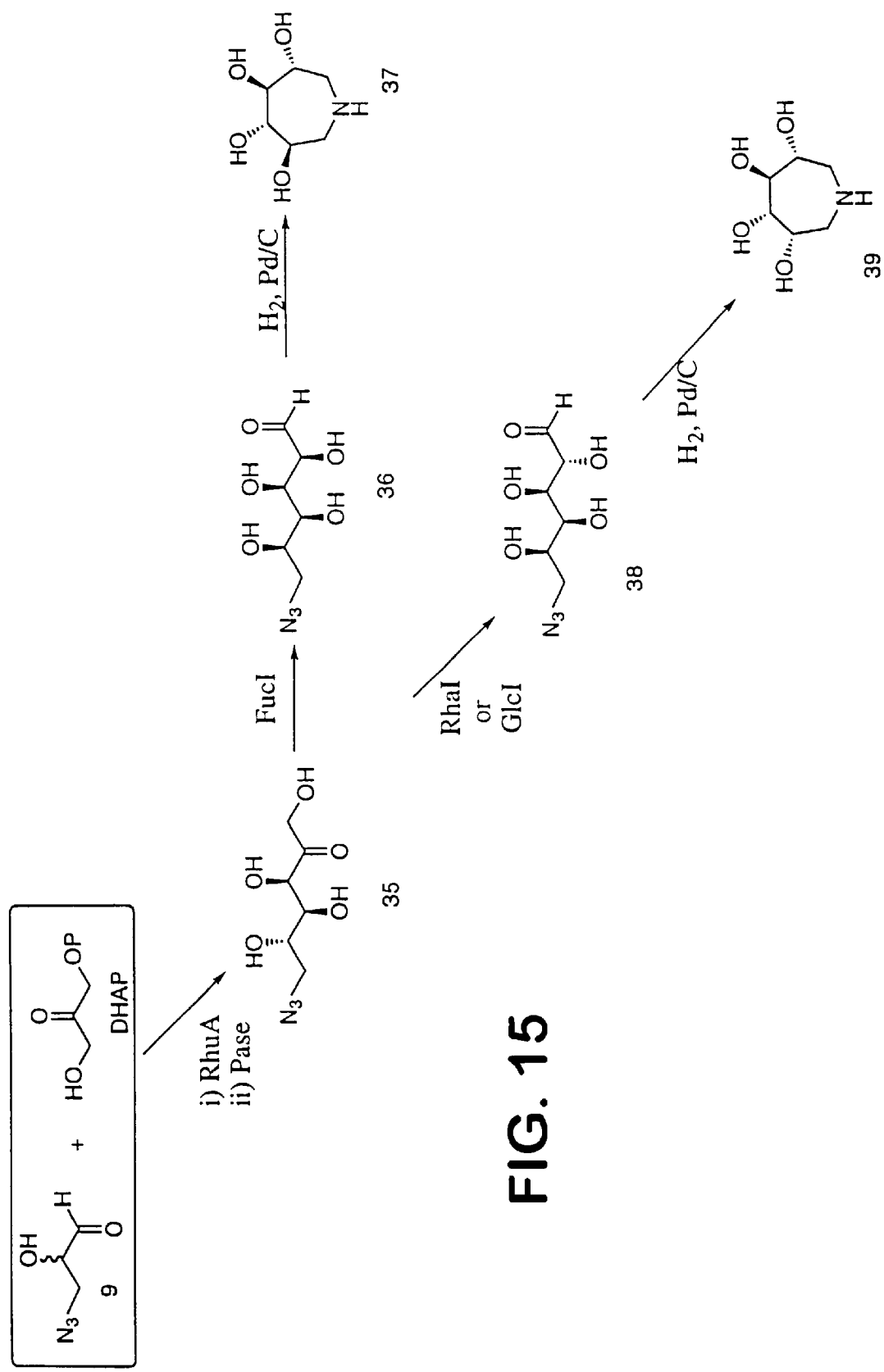

The X-ray crystal structure of a representative compound (7) was determined and shown to adopt a pseudo-chair conformation (FIG. 9) with bond lengths and angles for compound (7) shown in FIG. 10.

Figure 8:
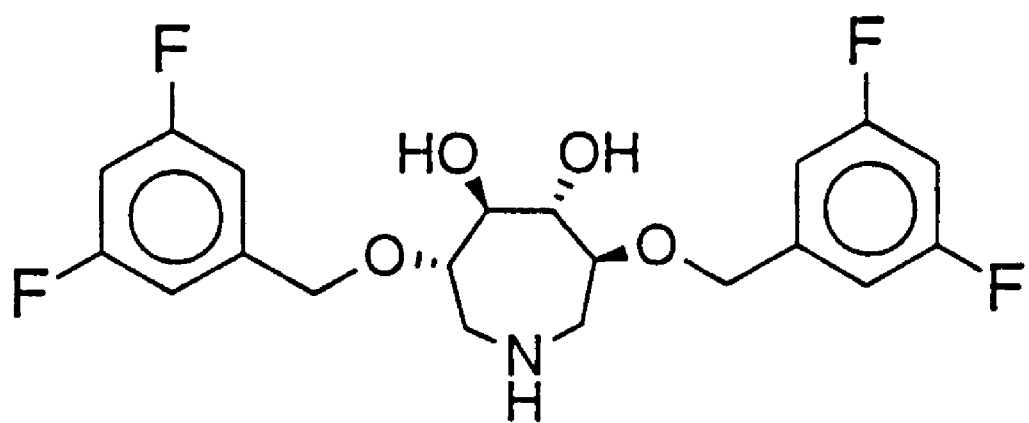
FIG. 8 illustrates the 3,6-dibenzyl derivative 60b which is a moderate inhibitor of the HIV protease with $K_i$ around 350 $\mu$M.

The synthesized iminocyclitols were also tested as inhibitors of a mechanistically related enzyme, i. e. the HIV protease. The 3,6-dibenzyl derivatives, especially 60b (illustrated in FIG. 8), are, moderate inhibitors of the HIV protease with $K_i$ around 350 μM. Interestingly, these benzyl derivatives were not inhibitors of the glycosidases.

It is known that symmetrical seven-membered ring cyclic urea (Lam et al. *Science* 1994, 263, 380), cyclic oxamide (Jadhav et al. *Tetrahedron Lett.* 1996, 37, 1153; Sham et al. *J. Med. Chem.* 1996, 39, 392), and non-symmetric azacyclic urea (Sham et al. *J. Med. Chem.* 1996, 39, 392) are very good inhibitors for HIV protease. Compounds 3, 6, 8 and 7 were, however, not inhibitors of these proteases. We then investigated the protected derivatives. 3-Fluorobenzyl or 3,5-difluorobenzyl groups were introduced to the 3- and 6-OHs by treating 50 with sodium hydride followed by 3-fluorobenzyl bromide or 3,5-difluorotoluene to give compounds 59a and 59b (FIG. 19), respectively. Here fluorinated benzyl groups were used in order to increase the water solubility of the final compounds. The benzyl derivatives that are attached to the 3- and 6-OHs in 60a and 60b may serve as binding motif to the P1 and P1' sites of the HIV/FIV proteases.

Compounds 60a, 60b, 64a, 64b, 65a, and 65b were tested for their inhibitory activities against the HIV and FIV protease (Tith et al. *Int. J. Peptide Protein Res.* 1990, 36, 544; Slee et al. *J. Am. Chem. Soc.* 1995, 117, 11867). The results are listed in FIG. 20. Generally, all compounds that were assayed have an $IC_{50}$ value in the upper micromolar range against both proteases. Tetrahydroxyazepanes 3 and 6 did not show inhibitory activities for the HIV protease. This may indicate that the lipophilic moieties introduced to the 3,6-OHs are crucial for enzyme-inhibitor interactions. The reasons for the weak inhibition of the HIV protease by these compounds may be due to: (1) The lipophilic side chains in these compounds might be one bond further from the seven-membered ring scaffold, since all the reported inhibitors have the benzyl groups directly connected to the seven-membered ring scaffolds. Thus, the fluorobenzyl binding motifs may not have optimal interactions with the P1 and P1' sites as expected; (2) the lack of another set of lipophilc binding motif at the C2 and C7 positions may significantly decrease the binding affinity, thus the structural simplicity of these hydroxyazepanes do not compromise the structural demand for the HIV protease; (3) although there is a good hydrogen bond acceptor in compounds 65a and 65b, the extra N-methyl group may interfere with the interaction of the oxygen anion with the amide protons of the $Ile^{50}$ and $ILe^{50'}$; (4) these compounds also may interact with the HIV protease in a different orientation compared to the cyclic urea based inhibitors. Nonetheless, the inhibition of the HIV protease by these tetrahydroxyazepanes suggested that we may have a correct scaffold. The lipophilic motif should be optimized in order to achieve tight binding.

In the inhibition of FIV protease, we observed a similar trend. Most of the N-substituted compounds 64a, 64b, 65a, and 65b did not show inhibition (FIG. 20), compounds 60a and 60b were active, however, their $IC_{50}$ values were inceased compared to their inhibitory activity to the HIV protease. This observation is in agreement with the α-ketoamide based inhibitors reported previously (Slee et al. *J. Am. Chem. Soc.* 1995, 117, 11867). Interestingly, compounds 60a, 60b, 64a, 64b, 65a, and 65b are not inhibitors of the glycosidases.

In summary, we have invented novel chemo and chemo/enzymatic methodologies toward the syntheses of various seven-membered iminocyclitols which have been shown to be a new class of glycosidase inhibitors and which may be useful as new templates for the development of HIV protease inhibitors.

Experimental Protocals

General

Materials and Methods

Rabbit muscle aldolase (E.C. 4.1.2.13) and acid phosphatase (E.C. 3.1.3.2) were purchased from Sigma. The enzymes fuculose-1-phosphate aldolase, rhamnulose-1-P-aldolase, fucose isomerase and rhamnose isomerase were prepared in our laboratory as described previously (Henderson et al. *Bioorg. Med. Chem* 1994, 2, 837; Garcia-Junceda et al. *Bioorg. Med. Chem.* 1995, 3, 1349). Benzyl α-D-mannopyranoside was purchased at Toronto Research Chemicals Inc., diphenylphosphoryl azide at Fluka and the remainder of the chemicals and solvents were purchased from Aldrich and used without further treatment. Dowex 50W-X8 (Biorad, 200–400 mesh, $H^+$ form) was converted to $NH_4^+$ form by passing 2N ammonium hydroxyde and thoroughly washed with purified water prior to use. Aldol condensation was monitored enzymatically by DHAP consumption (Bergmeyer et al. *Methods of Enzymatic Analysis,* 3rd Ed., Vol 2, Verlag Chemie: Deerfield, Fla., 1984, pp 146). The phosphatase-catalyzed hydrolysis was monitored by TLC (silica gel 60 from Merck). Isomerization was monitored by $^{13}$C-NMR (100 MHz) analysis of the anomeric center in the cyclized form. Nuclear magnetic resonance ($^1$H: 400 MHz; $^{13}$C: 100 MHz) spectra were obtained using $D_2O$ (δ=4.65 ppm) or $CD_3OD$ (δ=3.5 ppm for $^1$H and 49.9 for $^{13}$C). Flash chromatography was carried out with silica gel 60 (230–mesh). Inhibitory analysis were performed on a Beckman DU-70 spectrophotometer at 400 nm.

Synthesis of (3R,4R,5R,6S)-tetrahydroxyazepane (1) as Illustrated in FIG. 2

Steps (a–b; FIG. 2)

3-azido-2-hydroxypropanaldehyde 9 was formed in situ as follows: the diethyl acetal of 9 (1.512 g; 8 mmol; synthesized according to von der Osten C et al. *J. Am. Chem. Soc.,* 1989, 111, 3924) was dissolved in water (3 mL) and Dowex 50W-X8 (H+ form, 200–400 mesh) was added until pH<2. The mixture was heated at 50° C. for 8 hours, then the resin was filtered off and washed with water. A solution of DHAP (250 mM, 15 mL, 3.8 mmol; dihydroxyacetone phosphate; Aldrich/Sigma) was added and the mixture was adjusted to pH 6.8 with 6N NaOH. Rabbit muscle aldolase, RAMA (840 μL, 300 units; Sigma) was added, the mixture was stirred gently at room temperature until DHAP analysis indicates >90% conversion and the pH was adjusted to 4.7 with HCl. Acid phosphatase (780 μL, 300 units—see materials/methods—supra) was added and the mixture heated at 37° C. until the organic phosphate was hydrolyzed completely as indicated by TLC analysis (EtOH:NH$_4$OH, 1:1). 6-Azido-6-deoxyfructose was purified by silica gel chromatography (CH$_2$Cl$_2$:MeOH, 6:1) to yield 465 mg (61%) of a product with data in accordance with the reported previously (Straub et al. *J. Org.Chem.* 1990, 55, 3926).

Step (c): Synthesis of Compound 10 (FIG. 2)

70 mg of this product were disolved in 2 mL Tris buffer (50 mM, 2 mM Mn$^{2+}$, pH=7.7; Sigma) and 200 mg of immobilized glucose isomerase (TAKASWEET; Miles Labs) were added. The mixture was shaken at 37° C. for 24 hours. $^1$H- and $^{13}$C-NMR analysis indicated the presence of a mixture of aldose 10 and ketose ($^-$65:35). The enzyme was filtered off and solvent evaporated under reduced pressure, and the residue chromatographed carefully on silica gel (CHCl$_3$:MeOH, 6:1) to yield 30 mg (42%, 26% overall) of 6-azido-6-deoxyglucopyranose 10. Spectral data are in agreement with those reported previously (Durrwachter et al. *J. Org. Chem.* 1988, 53, 4175).

Step (d)

Azidoaldose 10 (vida supra) was hydrogenated at 50 psi in water using Pd/C as catalyst (0.10 equivalents). The reaction was monitored by NMR and was complete after 48 hours. The catalyst was removed by filtration and the solvent evaporated under reduced pressure. (3R,4R,5R,6S)-tetrahydroxyazepane 1 was obtained in 94% yield (24% overall): $^1$H-NMR (D$_2$O, δ, ppm): 3.85 (1H, ddd, J=1.7 Hz, 3.6 Hz, 5.4 Hz, H3 or H6); 3.59 (2H, m, overlapped H4+H5); 3.48 (1H, q, J=5.5 Hz, H3 or H6); 2.7–2.8 (4H, dd, J=14.5 Hz, 5.4 Hz) and d (J=5.4 Hz) overlapped 2H2+2H7). $^{13}$C-NMR (D$_2$O, δ, ppm): 75.18, 74.62, 73.28, 71.21, 69.30, 49.46, 49.20. MS (FAB+), (M+H) expected 164.0923, observed 164.0920.

Synthesis of 6-azido-6-deoxyrhamnulose (11) as illustrated in FIG. 2

3-azido-2-hydroxypropanaldehyde 9 (diethyl acetal, 284 mg; 1.5 mmol; synthesized according to von der Osten C et al. *J. Am. Chem. Soc.,* 1989, 111, 3924) was mixed with a solution of DHAP (230 mM, 4.34 mL, 1 mmol; Sigma) was added and the mixture was adjusted to pH 6.8 with 6N NaOH, followed by addition of rhamnulose-1-phosphate aldolase (270 μL, 10 units; Sigma). After 24 h DHAP analysis indicated 95% conversion and the pH was adjusted to 4.7 with HCl. Acid phosphatase (200 μL, 100 units—see materials and methods, supra) was added and the mixture heated at 37° C. until the organic phosphate was hydrolyzed completely as indicated by TLC analysis (EtOH:NH$_4$OH, 1:1). 6-Azido-6-deoxyrhamnulose 11 was purified by silica gel chromatography (CHCl$_3$:MeOH, 6:1) to yield 60 mg (30%). Spectral data are the same as for the enantiomeric fructose analog (Straub et al. *J. Org.Chem.* 1990, 55, 3926) with opposite sign for the optical rotation $[\alpha]_{25D}$=−8.9 (c=1.95, MeOH). Several attemps to isomerize this product in 2 mL Tris buffer (50 mM, 2 mM Mn$^{2+,}$ pH =7.7) and in presence of variable amounts of rhamnose isomerase were unsuccesful. The mixture was shaken at 37° C. and the reaction monitored by $^1$H- and $^{13}$C-NMR, no aldose peaks were detected even after 3 days.

Synthesis of (3S,4R,5S,6R)-tetrahydroxyazepane Compound 2 as Illustrated in FIG. 2

Enzymatic synthesis: 3-azido-2-hydroxypropanaldehyde 9 (diethyl acetal, 756 mg; 4 mmol; vida supra) was mixed with a solution of DHAP (262 mM, 7.6 mL, 2 mmol) at pH 6.5. Fuculose-1-phosphate aldolase was added (640 μL, 10 units—see materials and methods, supra) and the mixture was stirred at room temperature. After 18 h DHAP analysis indicated 91% conversion and the pH was adjusted to 4.7 with HCl. Acid phosphatase (200 μL, 100 units—see materials and methods, supra) was added and the mixture heated at 37° C. until the organic phosphate was hydrolyzed completely as indicated by TLC analysis (EtOH:NH$_4$OH, 1:1). After deprotection of the phosphate, 6-Azido-6-deoxyfuculose was isolated by Dowex-50W (Ba$^{2+}$ form 3×20 cm) chromatography (Liu et al. *J Chem Soc Perkin Trans I* 1991, 1991, 2669) using water as eluent to yield 99 mg (25%). $^1$H-NMR (D$_2$O, δ, ppm, major anomer only): 4.15 (1H, t, J=4.5 Hz, H4); 4.05 (1H, d, J=4.5 Hz, H3); 4.00 (1H, m, J=2 Hz, 4.5 Hz, 8.5 Hz, H5); 3.3–3.5 (4H, m, overlapped signals, 2H1 and 2H6). $^{13}$C-NMR (D$_2$O, δ, ppm): 102.78, 78.43, 70.96, 70.43, 62.45, 50.99 (major), 105.16, 77.65, 76.88, 71.29, 62.22, 50.32 (minor). MS (FAB+), (M+) expected 205.0699, observed 205.0691.

Step (h) FIG. 2

This product was dissolved in 2 mL Tris buffer (50 mM, 2 mM Mn$^{2+}$, pH=7.7) and 1200 units (2 mL) of fucose isomerase (see materials and methods section were added. The mixture was stirred at room temperature for 24 hours. $^1$H- and $^{13}$C-NMR analysis indicated the consumption of the ketose and the appearence of a new compound, aldose 12 ($^-$95:5). The enzyme was precipitated with acetone and solvent evaporated under reduced pressure, the residue was chromatographed on Dowex-50W (Ba$^{2+}$ form, 3×20 cm) using EtOH:H$_2$O 1:1 as eluent to yield 82 mg (82%, 21% overall) of 6-azido-6-deoxy-L-fucopyranose 12. The NMR data were the same that reported previously (Wong et al. *J. Org. Chem.* 1995, 60, 7360).

Step (d) FIG. 2

To a solution (H$_2$O:THF 3:1, 4 mL) of 12 (60 mg) was added a catalytic amount of Pd/C (approx. 0.10 equivalents) is added and the mixture is hydrogenated at 50 psi. After 20 hours of reaction azasugar 2 was obtained as the major product but NMR analysis also showed another minor compound, characterized as 8-oxa-[3.2.1]-2-aza-4,6,7triol-bicycloheptane 17: $^1$H-NMR (CD$_3$OD, δ, ppm): 4.92 (1H, d, J=6 Hz; 4.36 (1H, d, J=2.5 Hz); 4.32 (1H, ddd, J=1 Hz, 2.5 Hz, 6 Hz); 4.09 (1H, d, J=4.3 Hz); 3.91 (1H, m); 3.18 (1H, ddd, J=1 Hz, 8.8 Hz, 13.5 Hz) and 2.87 (1H, dd, J=13.5 Hz, 10.8 Hz). $^{13}$C-NMR (CD$_3$OD, δ, ppm) : 89.03, 87.18, 82.43, 79.05, 66.64, 46.67. After additional period of time ($^-$2 d) the bicyclic compound disappeared completely and (3S,4R, 5S,6R)-tetrahydroxyazepane 2 was the only product detectable (55 mg, 91%, 19% overall) $^1$H-NMR (D$_2$O, δ, ppm): 3.82 (2H, d, J=6.5 Hz, H4+H5); 3.66 (2H, dd, J=4.5 Hz, 6.1 Hz, H3+H6); 2.77–2.67 (4H, dd, J=14.8 Hz, 4.5 Hz, 2H2+ 2H7). $^{13}$C-NMR (D$_2$O, δ, ppm): 74.28, 70.90, 51.43. MS (FAB+), (M+H) expected 164.0923, observed 164.0918.

(3S,4R,5S,6R)-tetrahydroxyazepane 2: Chemical Synthesis as Illustrated in FIG. 3.

Step (a: i–ii)

To a solution of 1,2:3,4-diisopropylidene-D-galactose 13 (3.67 g, 14.1 mmol; obtained by refluxing D-galactose in 0.10 Molar dry acetone with 0.10 equivalents Camphor Sulphonic Acid—CSA, followed by standard workup conditions) in THF (30 mL) at 0° C., DEAD (2.26 mL, 14.1 mmol; diethylazodicarboxylate; Aldrich) and PPh$_3$ (3.79 g, 14.1 mmol; triphenylphosphine; Aldrich) were added and the mixture stirred for 15 minutes. Then, diphenylphosphoryl azide (3.04 mL, 14.1 mmol; Aldrich) was added dropwise and the reaction mixture stirred overnight. The solvent was evaporated under reduced pressure and the product was purified by silica gel chromatography (CH$_2$Cl$_2$) to yield 3.25 g (80%) of 6-azido-6-deoxy-1,2:3,4-diisopropylidene-D-galactose. $^1$H-NMR (CDCl$_3$, δ, ppm): 5.51 (d, J=5 Hz, H1); 4.60 (dd, J=1.5 Hz, J=8 Hz, H3); 4.30 (dd, J=1.5 Hz, J=5 Hz, H2); 4.15 (dd, J=2 Hz, J=8 Hz, H4); 3.90 (ddd, J=2 Hz, J=5 Hz, J=7.5 Hz, H5); 3.50 (dd, J=12.5 Hz, J=7 Hz, H6); 3.35 (dd, J=12.5 Hz, J=5 Hz, H6'). $^{13}$C-NMR (CDCl$_3$, δ, ppm): 110.23, 109.43, 26.13, 26.04, 24.98, 24.51 (isopropylidene), 96.88, 71.53, 71.16, 70.74, 67.36, 50.91 (sugar).

Steps (b–c)—FIG. 3

The above compound was treated with 80% AcOH at 70° C. during 3 hours (TLC showed completion, CH$_2$Cl$_2$:MeOH, 4:1). The solvent was removed in vacuo to yield 6-azido-6-deoxygalactose 14 (2.15 g, 95%), the spectral data are the same as those reported for the enantiomer (Wong et al. *J. Org. Chem.* 1995, 60, 7360). This product (60 mg) was hydrogenated at 50 psi in H$_2$O:THF 3:1 with a catalytic amount of palladium/carbon (0.10 equivalents) for 2 days to give (3S,4R,5S,6R)-tetrahydroxyazepane 2 (50 mg, 90%).

Synthesis of (3R,4R,5R,6R)-tetrahydroxyazepane 3 (FIG. 4)

Step (a)

To a solution of benzyl mannopyranoside 18 (500 mg, 1.9 mmol; Synthesized via reflux in dry 1.0 Molar benzyl alcohol with 0.01 equivalents CSA, the reaction mixture is passed through a SiO$_2$ column; benzyl alcohol comes out first using EtOAc:Hexane 1:5, then benzyl pyranoside is separated from the furanose byproduct with EtOAc as eluent) in dry pyridine (5 mL) at 0° C. was added tosyl chloride (381 mg, 2 mmol; Aldrich) dissolved in CH$_2$Cl$_2$ and the reaction was monitored by TLC (EtOAc). After 4 hours, the starting material was consumed completely. The reaction mixture was extracted with CH$_2$Cl$_2$ and washed with 1N HCl, sat. NaHCO$_3$ and brine, and purified by flash chromatography using EtOAc as eluent to yield 531 mg (68%) of benzyl 6-tosyl-6-deoxy-D-mannopyranoside.

Step (b) Synthesis of Compound 19

To a solution of this compound (120 mg, 0.29 mmol) in EtOH:H$_2$O 9:1 was added 5 equivalents of NaN$_3$ and 5 equivalents of NH$_4$Cl and this mixture was refluxed overnight, solvent is removed in vacuo and residue chromatographed in SiO$_2$ using EtOAc as eluent to yield benzyl 6-azido-6-deoxy-D-mannopyranoside, 19 (60 mg, 70%). $^{13}$C-NMR (CDCl$_3$, δ, ppm): 136.61, 128.43, 128.10, 127.99, 69.27 (benzyl group), 98.82, 71.53 (double intensity), 70.65, 68.14, 51.25.

Step (c). Synthesis of Compound 3

A solution of this product (26 mg, 0.09 mmol) in water (3 mL) was added 20 mg of Pd/C and hydrogenated at 50 psi during 24 hours. The catalyst was removed by filtration and the filtrate purified by ion-exchange chromatography (Dowex-50W, NH$_4$+ form, 1×20 cm) eluted first with water and then with a NH$_4$OH gradient 0→1N. The fractions containing the product were pooled and HCl was added to form the hydrocloric acid salt of (3R,4R,5R,6R)-tetrahydroxyazepane 3 (16 mg, 85%):(Poitout et al. *Tetrahedron Lett.* 1994, 35, 3293). $^1$H-NMR (D$_2$O, δ, ppm): 4.15 (2H, m, H4+H5); 3.70 (2H, s, H3+H6); 3.25 (4H, dd, J=14.4 Hz, 6.4 Hz, 2H2+2H7). $^{13}$C-NMR (D$_2$O, δ, ppm): 73.26, 67.03, 45.13.

Synthesis of (6R)-acetamido (3S,4R,5S) trihydroxyazepane 4 as Illustrated in FIG. 4

To 11 g of N-acetyl-glucopyranose 20 (Sigma) was added 68 mL benzyl alcohol and HCl gas was passed for 3 minutes. The mixture was allowed to react for 3 hours and the precipitate is collected and washed with cold water, cold ether and hexane (yield 30%). This benzyl N-acetyl-glucosamine pyranoside (500 mg, 1.67 mmol) was subjected to the same sequence as that of compound 18 above, to yield benzyl 6-azido-6-deoxy-N-acetylglucosamine pyranoside (241 mg, 43% overall yield) 21: $^{13}$C-NMR: (CD$_3$OD, δ, ppm, α-anomer only): 175.68, 23.68 (acetamide); 140.61, 131.27, 131.15, 130.78, 71.89 (benzyl group); 99.09, 74.64 (double intensity), 73.89, 56.62, 54.03 (sugar moiety). A sample of this compound (34 mg, 0.1 mmol) was hydrogenated over Pd/C in H$_2$O:THF 4:1 overnight and the azasugar 4 purified by ion-exchange chromatography (Dowex-50W, NH$_{4+}$ form, 1×20 cm) eluted first with water and then with a NH$_4$OH gradient 0→1N. The fractions containing the product were pooled and HCl was added to form the hydrocloric acid salt of (6R)-acetamido (3S,4R,5S) trihydroxyazepane 4 (14 mg, 60%: $^1$H-NMR (D$_2$O, δ, ppm): 4.15 (1H, dt, J=2 Hz, 6.5 Hz, H3); 3.87 (1H, dt, J=3 Hz, 8 Hz, H6); 3.68 (1H, t, J=8 Hz, H5); 3.59 (dd, J=2 Hz, 8 Hz, H5); 3.32–3.12 (4H, m, 2H2+2H7). $^{13}$C-NMR (D$_2$O, δ, ppm): 75.23, 72.05, 66.83, 49.28, 45.73, 45.18, 21.86.

Synthesis of (3S,4R,5S,6R)-3-methoxy-4,5,6-trihydroxyazepane 5 as Illustrated in FIG. 5

A suspension of 6-azido-6-deoxy-D-galactose 14 (1.63 g, 7.9 mmol) obtained as describe above in benzyl alcohol (5 mL) was heated to 80° C. and BF$_3$.OEt$_2$ (984 μL, 8 mmol) was added dropwise. After 20 minutes the suspension became transparent. The solution was allowed to cool down. The reaction mixture was passed through a SiO$_2$ column. Benzyl alcohol came out first using EtOAc:Hexane 1:5, then benzyl 6-azido-6-deoxy-D-galactopyranoside was separated from the furanose byproduct with EtOAc as eluent (1.21 g, 75%, α/β 60:40): $^1$H-NMR (CD$_3$OD, δ, ppm, α-anomer only): 7.4–7.6 (5H, Benzyl group); 5.3 (H1, overlapped by HDO signal); 4.98 and 4.78 (2H, AB system, J=12 Hz, CH$_2$—OBn); 4.18 (1H, dd, J=4.2 Hz, 8.7 Hz, H5); 4.0 (3H, overlapped, H2, H3, H4); 3.75 (1H, dd, J=13 Hz, 8.7 Hz, H6); 3.49 (1H, dd, J=13 Hz, 4.2 Hz, H6'). $^{13}$C-NMR (CD$_3$OD, δ, ppm, α-anomer only): 139.76, 131.64, 130.31, 100.28, 72.54, 72.36, 72.10, 71.36, 70.89, 53.62.

Step (b) FIG. 5

To a solution of this product (400 mg, 1.35 mmol) in DMF (4 mL) was added 2,2-dimethoxypropane (1 mL, large excess) and a catalytic amount of p-tosylic acid. The reaction was driven overnight under argon at room temperature and then extracted with Et$_2$O. Further purification by flash chromatography (EtOAc:Hexanes 1:1) yielded 429 mg (95%) of benzyl 6-azido-6-deoxy-3,4-isopropylidene-D- galactopyranoside, 22. $^{13}$C-NMR (CDCl$_3$, δ, ppm, α-anomer only): 136.81, 128.43, 128.32, 128.11, 69.68 (benzyl group); 109.73, 27.33, 25.62 (isopropylidene); 96.15, 75.49, 73.06 (double), 68.65, 68.12, 51.13 (sugar).

Steps (c–d) FIG. 5:

To a solution of this latter product (204 mg, 0.6 mmol) in dry THF (5 mL) was added MeI (38.6 μL, 0.62 mmol) and NaH (16 mg, 0.66 mmol), the mixture was reacted at room temperature for 2 hours, then was extracted with CH$_2$Cl$_2$ and the resulting syrup treated with 80% AcOH at 70° C. for 3 hours. Evaporation of the solvent with added water (3 times) yielded 163 mg (88% from 22) of benzyl-6-azido-6-deoxy-2-O-methyl-D-galactopyranose 23: $^1$H-NMR (CD$_3$OD, δ, ppm, α-anomer only): 7.4–7.6 (5H, Benzyl group); 5.28 (1H, d, J=3.7 Hz, H1); 4.95 and 4.75 (2H, AB system, J=12 Hz, CH$_2$—OBn); 4.15 (1H, dd, J=4 Hz, 8.8 Hz, H5); 4.05 (1H, dd, J=3.4 Hz, 10 Hz, H3); 3.85 (1H, d, J=3.4 Hz, Hr); 3.75 (1H, dd, J=13 Hz, 8.7 Hz, H6); 3.45 (1H, dd, J=13 Hz, 4 Hz, H6'); 3.68 (1H, dd, J=10 Hz), 3.7 Hz, H2); 3.60 (3H, s, MeO-). $^{13}$C-NMR (CD$_3$OD, δ, ppm, α-anomer only): 140.51, 131.22, 130.73, 97.87, 80.66, 72.87, 72.78, 71.67, 71.59, 59.69, 53.98.

Step (e) FIG. 5

A sample of this product (105 mg, 0.34 mmol) was hydrogenated at 50 psi over Pd/C (0.10 equivalents) in water (0.10 Molar) over 48 hours to yield (3S,4R,5S,6R)-3-methoxy-4,5,6-trihydroxyazepane 5 (54 mg, 90%): $^1$H-NMR (D$_2$O, δ, ppm): 4.29 (1H, dd, J=1.3 Hz, 6.3 Hz, H4 or H5); 4.09 (1H, dd, J=1.3 Hz, 7.1 Hz, H5 or H4); 3.97 (1H, dt, J=4.5 Hz, 7.1 Hz, H3 or H6); 3.5 (4H, Me and H6 or H3 overlapped by Me); 3.27 (1H, dd, J=14.3 Hz, 4.5 Hz, H2 or H7); 3.27 and 2.03 (1H each, dd, J=14.3 Hz, 4.4 Hz, 2×H2 or 2×H7); 3.7 and 4.1 (1H each, dd, J=14.3 Hz, 4.4 Hz, 2×H2'or 2×H7'). $^{13}$C-NMR (D$_2$O, δ, ppm): 83.99, 77.04, 75.33, 73.66, 58.67(OMe), 54.78, 50.85. MS (FAB+), (M+H) expected 178.1079, observed 178.1072.

Figure 6:
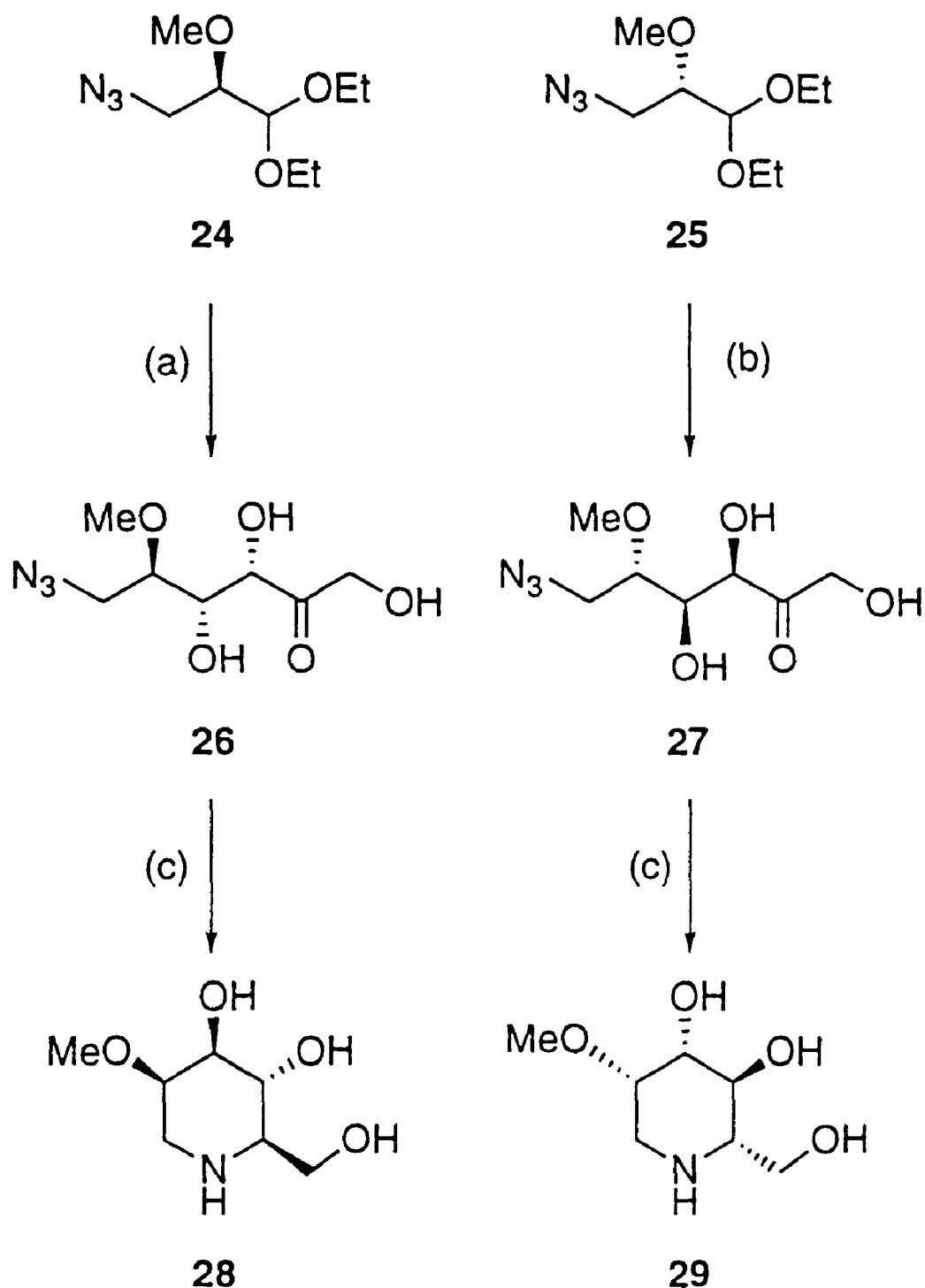
FIG. 6 illustrates the chemo/enzymatic synthesis of tetrahydroxy azepanes 28 and 29 wherein the indicated steps are as follows: (a) (i) pH=6.7, DHAP, FDPA (fructose-1,6-diphosphate aldolase); (ii) pH=4.5, Pase (Acid phosphatase); (b)(i) pH=6.7, DHAP, RhaA (rhamnulose-1-phosphate aldolase); (ii) pH=4.5, Acid Pase (Acid phosphatase); (c) $H_2$, 50 psi, room temperature, MeOH, 3 hours, 90–95%.

Synthesis of (3S,4R,5S)-6-azido-5-methoxy-1,3,4-trihydroxyhexan-2-one Compound 26 (FIG. 6)

A solution of 3-azido-2(R)-methoxy-propanal diethyl acetal 24 (934 mg, 4.6 mmol) prepared by methylation of 3-azido-2(R)-hydroxy-propanal diethyl acetal obtained enzymatically; von der Osten, C. H.; Barbas, C. F.; Wong, C. H.; Pederson, R. L.; Sinskey, A. J.; Wang, Y. F. *J. Am. Chem. Soc.* 1989, 111, 3924) was dissolved in water (5 mL) and Dowex 50W-X8 (H$^+$ form, 200–400 mesh) was added until pH <2. The mixture was heated at 50° C. for 8 hours, then the resin was filtered off and washed with a minimum amount of water. A solution of DHAP (262 mM, 7.6 mL, 2 mmol) was added and the mixture was adjusted to pH 6.5 with 6N NaOH. Fructose-1,6-diphosphate aldolase was added (1.4 mL, 500 units; see general section—supra) and the mixture was stirred at room temperature. After 4 h the pH was adjusted to 4.7 with HCl. Acid phosphatase (500 μL, 400 units—see general materials section, supra) was added and the mixture heated at 37° C. The enzyme was precipitated by adding acetone and these residue evaporated and chromatographed on SiO$_2$ (CH$_2$Cl$_2$:MeOH 6:1), to give 400 mg (40%) of (3S,4R,5S)-6-azido-5-methoxy-1,3,4-trihydroxyhexan-2-one 26: $^1$H-NMR (D$_2$O, δ, ppm) 4.48 and 4.35 (1H each, J=19.8 Hz, H1 and H1'); 4.38 (1H, d, J=3 Hz, H3); 3.85 (1H, dd, J=9.2 Hz, 1.9 Hz, H4), 3.7 (1H, dd, J=13.6 Hz, 2.8 Hz, H6); 3.45, (1H, ddd, J=9.2 Hz, 2.8 Hz, 3.7 Hz, H5); 3.33 (3H, s, Me); 3.30 (1H, dd, 13.5 Hz, 3.7 Hz, H6'). $^{13}$C-NMR (D$_2$O, δ, ppm): 213.22, 78.55, 74.85, 70.26, 65.98, 57.36, 48.97.

Synthesis of (3R,4S,5S)-6-azido-5-methoxy-1,3,4-trihydroxyhexan-2-one 27 (FIG. 6)

A solution of 3-azido-2(S)-methoxy-propanal diethyl acetal 25 (832 mg, 4.1 mmol) prepared in the same way as above for compound 26 from the S-enatiomer was treated in the same manner as described for the R enantiomer. In this case rhamnulose-1-phosphate aldolase was added (0.5 mL, 80 units) and after usual monitoring and work-up, 380 mg (38%) of (3R,4S,5S)-6-azido-5-methoxy-1,3,4-trihydroxyhexan-2-one 27 were obtained. The NMR data were identical to those of 26.

Synthesis of 2-O-methyl-1-deoxy-D-mannojirimycin 28 (FIG. 6)

A sample of 26 (39 mg, 0.17 mmol) was hydrogenated in MeOH (2mL) over Pd/C (0.10 equivalents) at 50 psi for 3 hours. After filtering the catalyst off and evaporating the solvent, 29 mg (95%) of 2-O-methyl-1-deoxy-D-mannojirimycin 28 were obtained: $^1$H-NMR (CD$_3$OD, δ, ppm): 3.91 (1H, dd, J=4.5 Hz, 11.1 Hz, H6); 3.96 (1H, J=11.1 Hz, 3 Hz, H6'); 3.75 (1H, t, J=9.6 Hz, H4); 3.65 (1H, ddd, J=2.7 Hz, 2.8 Hz, 1.2 Hz, H2); 3.60 (4H, Me and H3 overlapped by Me); 3.40 (1H, dd, J=14 Hz, 2.7 Hz, H1); 2.75 (1H, dd, J=14 Hz, 1.2 Hz, H1'); 2.55 (1H, ddd, J=9.7 Hz, 4.4 Hz, 3.2 Hz, H5). $^{13}$C-NMR (CD$_3$OD, δ, ppm): 178.58, 74.50, 68.08, 60.52, 59.88, 55.44, 43.71.

Synthesis of 2-O-methyl-1-deoxy-L-mannojirimycin 29

By using the same procedure as above for the D-enantiomer, 120 mg of 27 gave 88 mg (90%) of 2-O-methyl-1-deoxy-L-mannojirimycin 29, with NMR data identical to those of 28.

General Chemo/Enzymatic Synthesis of Hydroxyazepanes as Illustrated in FIGS. 11–15 (Synthesis of Compounds 1, 2, 3, 32, 37, 39, 42 and 44 (Steps a–d: infra)

Steps (a–b; FIGS. 11–15)

3-Azido-2-hydroxypropanaldehyde 9 is formed in situ as follows: the diethyl acetal of 9 (1.512 g; 8 mmol; synthesized according to von der Osten C et al. *J. Am. Chem. Soc.*, 1989, 111, 3924) is dissolved in water (3 mL) and Dowex 50W-X8 (H$^+$ form, 200–400 mesh) is added until pH<2. The mixture is heated at 50° C. for 8 hours, then the resin was filtered off and washed with water. A solution of DHAP (250 mM, 15 mL, 3.8 mmol; dihydroxyacetone phosphate; Aldrich/Sigma) is added and the mixture is adjusted to pH 6.8 with 6N NaOH. An aldolase selected from the group consisting of rhamnulose-1-phosphate aldolase, rabbit muscle aldolase, fructose-1,6-diphosphate aldolase and fucose aldolase(840 μL, 300 units; Sigma) is added, the mixture is stirred gently at room temperature until DHAP analysis indicates >90% conversion and the pH is adjusted to 4.7 with HCl. Acid phosphatase (780 μL, 300 units—see materials/methods—supra) is added and the mixture heated at 37° C. until the organic phosphate is hydrolyzed completely as indicated by TLC analysis (EtOH:NH$_4$OH, 1:1). Intermediate ketose is purified by silica gel chromatography (CH$_2$Cl$_2$:MeOH, 6:1).

Step (c): (FIGS. 11–15)

70 mg of this product are disolved in 2 mL Tris buffer (50 mM, 2 mM Mn$^{2+}$, pH=7.7; Sigma) and 200 mg of isomerase (isomerase selected from the group consisting of rhamnose isomerase, fucose isomerase, glucose isomerase and galacatose isomerase) is added. The mixture is shaken at 37° C. for 24 hours. $^1$H- and $^{13}$C-NMR analysis indicates the presence of a mixture of aldose 10, 34, 31, 12, 36, 38, 41 or 43 and ketose (~65:35: compound dependes on which enzyme is used in steps a–b (supra) to achieve the desired compound). The enzyme is filtered off and solvent evaporated under reduced pressure, and the residue chromatographed carefully on silica gel (CHCl$_3$:MeOH, 6:1) to yield pyranose 10, 34, 31, 12, 36, 38, 41 or 43.

Step (d)

Azidoaldose 10, 34, 31, 12, 36, 38, 41 or 43 (vida supra) is hydrogenated at 50 psi in water using Pd/C as catalyst (0.10 equivalents). The reaction is monitored by NMR and was complete after 48 hours. The catalyst is removed by filtration and the solvent evaporated under reduced pressure; the residue chromatographed carefully on silica gel (CHCl$_3$:MeOH, 6:1) to yield the hydroxyazepanes: COMPOUNDS 1, 2, 3, 32, 37, 39, 42 and 44.

Figure 16:
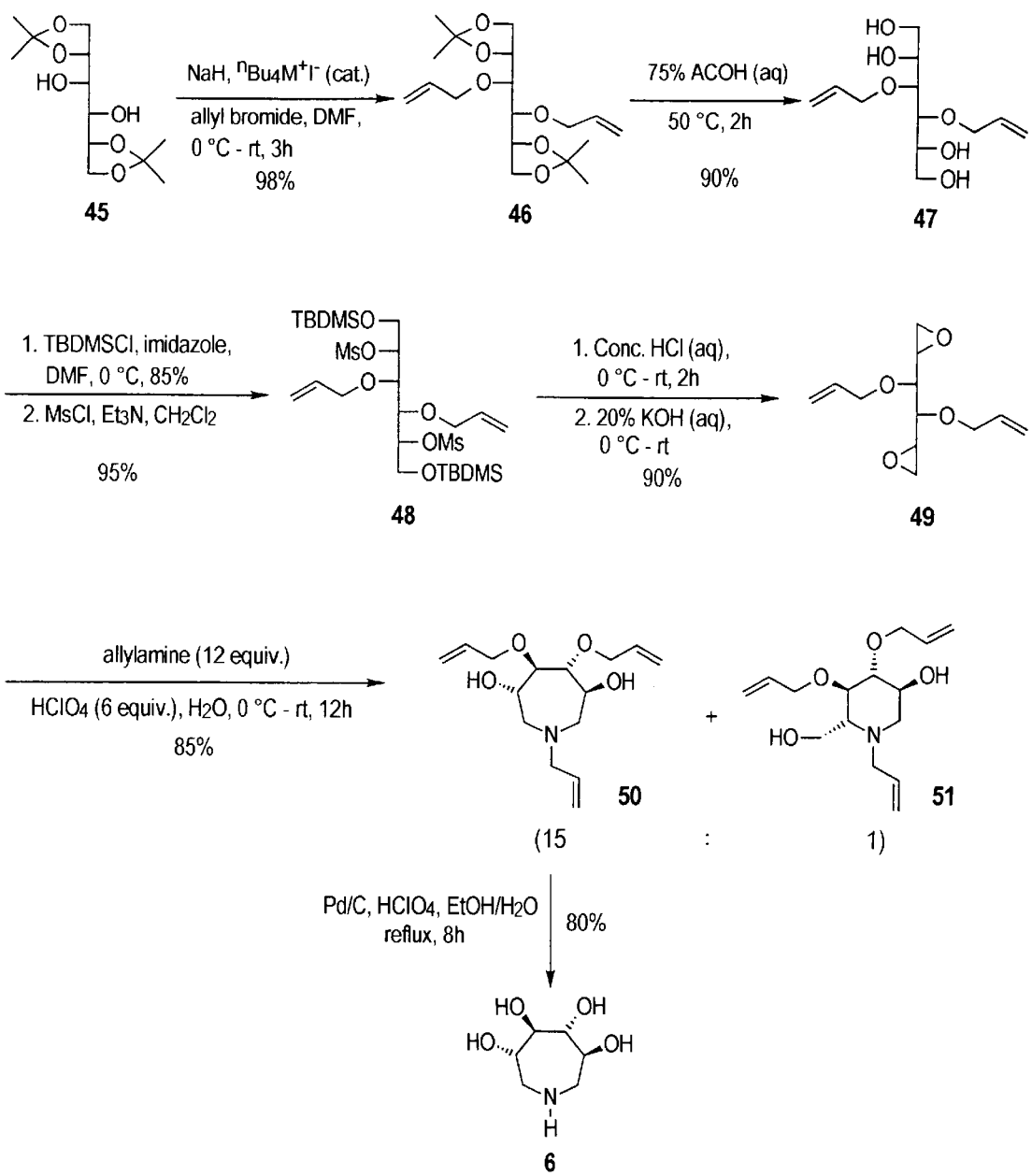
FIG. 16 illustrates the chemical synthesis of tetrahydroxy azepane 6.

Synthesis of 3,4-di-O-Allyl-1,2:5,6-di-O-isopropylidene-D-mannitol (46) as Illustrated in FIG. 16

To a stirred solution of 1,2:5,6-di-O-isopropylidene-D-mannitol (45, 10.0 g, 38 mmol) and tetrabutylammonium iodide (0.7 g, 1.9 mmol) in 150 anhydrous DMF at 0° C. was added sodium hydride (2.3 g, 91 mmol). The resulted gray suspension was allowed to stir at 0° C. for 30 minutes, followed by 15 minutes at room temperature. After cooling the suspension to 0° C., allyl bromide (20.0 mL, 231 mmol) was added slowly via a syringe. The resulting orange-brown suspension was stirred at 0° C. for 30 minutes, then warmed up to room temperature and stirred for an additional 1.5 hours. The reaction mixture was quenched at 0° C. by addition of 150 mL of saturated NaCl (aq) solution and was extracted with ethyl ether (200 mL×4). The combined organic layers were dried over anhydrous MgSO$_4$, filtered and concentrated to give a yellow-brownish oil. Chromatographic purification gave a yellow oil (12.8 g, yield 98%). R$_f$ 0.32 (EtOAc:hexanes=2:8, v/v). $^1$H NMR (250 MHz, CDCl$_3$) δ1.35 (6H, s), 1.41 (6H, s), 3.62 (2H, d, J=5.3 Hz), 3.96 (2H, dd, J=8.2 Hz, J'=6.6 Hz), 4.08 (2H, t, J=7.2 Hz), 4.20 (6H, m), 5.15 (2H, dd, J=11.3 Hz, J'=1.0 Hz), 5.25 (2H, dd, J=17.2 Hz, J'=1.5 Hz), 5.89 (2H, m) ppm. $^{13}$C NMR (CDCl$_3$) δ25.5, 26.7, 66.7, 73.9, 75.8, 79.8, 117.1, 134.7 ppm. FAB-HRMS Calcd for C$_{18}$H$_{31}$O$_6$: 343.2121. Found: [M+H]$^+$ 343.2133.

Synthesis of 3,4-di-O-Allyl-D-mannitol (47) as illustrated in FIG. 16

3,4-di-O-Allyl-1,2:5,6-di-O-isopropylidene-D-mannitol (46, 13.43 g, 39.2 mmol) was dissolved in 250 mL of a 75% acetic acid solution in water mixture (v/v). The resulting solution was heated to 50° C. and stirred for 2 hours. All volatiles were removed to give an off-white solid. The crude product was purified by column chromatography using a gradient of methanol from 4% to 12% in dichloromethane (v/v). The purified product was a white solid (9.3 g, yield 90%). R$_f$ 0.20 (methanol:dichloromethane=1:9, v/v). $^1$H NMR (400 MHz, CD$_3$OD) δ3.63 (2H, dd, J=11.1 Hz, J'=4.8 Hz), 3.73 (4H, m), 3.80 (2H, dd, J=11.1 Hz, J'=2.4 Hz), 4.14 (2H, dd, J=12.4 Hz, J'=5.8 Hz), 4.23 (2H, tdd, J=1.0 Hz, J'=5.6 Hz, J''=12.4 Hz), 5.11 (2H, dd, J=10.4 Hz, J'=1.3 Hz), 5.27 (2H, ddd, J=1.5 Hz, J'=3.1 Hz, J''=17.2 Hz), 5.95 (2H, m) ppm. $^{13}$C NMR (CD$_3$OD, TMS) δ64.6, 72.3, 74.7, 79.9, 116.8, 136.5 ppm. FAB-HRMS Calcd for C$_{12}$H$_{22}$O$_6$Na: 285.1314. Found: [M+Na]$^+$ 285.1320.

Synthesis of 3,4-di-O-Allyl-1,6-di-O-tert-butyldimethylsilyl-D-mannitol as Illustrated in FIG. 16

3,4-di-O-Allyl-D-mannitol (47, 6.77 g, 25.8 mmol) and imidazole (4.40 g, 64.6 mmol) were dissolved in 20 mL anhydrous DMF, and the solution was cooled to 0° C. tert-Butyldimethylsilyl chloride (9.13 g, 59.4 mmol) was added to the above solution in one portion while stirring. The reaction mixture was stirred at 0° C. for 2.5 hours. The reaction was quenched by addition of 15 mL of saturated NaHCO$_3$ (aq) solution and was then extracted with dichloromethane (60 mL×4). The combined organic layers were combined, dried, filtered and concentrated to give a light yellow oil. The product was further purified by column chromatography using a gradient of ethyl acetate from 7% to 10% in hexanes. The purified product was a light yellow oil weighing 12.41 g (yield, 98%). R$_f$ 0.56 (EtOAc:hexanes=3:7, v/v). $^1$H NMR (400 MHz, CDCl$_3$) δ0.10 (12H, s), 0.93 (18H, s), 2.66 (2H, d, J=6.1 Hz), 3.68 (2H, dd, J=4.4 Hz, J'=1.4 Hz), 3.81(6H, m), 4.12 (2H, tdd, J=1.3 Hz, J'=5.9 Hz, J''=12.4 Hz), 4.20 (2H, tdd, J=1.3 Hz, J'=5.8 Hz, J''=12.4 Hz), 5.14 (2H, ddd, J=1.2 Hz, J'=2.9 Hz, J''=10.3 Hz), 5.24 (2H, ddd, J=1.6 Hz, J'=3.3 Hz, J''=17.2 Hz), 5.93 (2H, m) ppm. $^{13}$C NMR (CDCl$_3$) δ−5.4, 18.3, 25.9, 63.9, 70.5, 73.4, 78.1, 117.0, 134.9 ppm. FAB-HRMS Calcd for C$_{24}$H$_{50}$O$_6$Si$_2$Na: 513.3044. Found: [M+Na]$^+$ 513.3020.

Synthesis of 3,4-di-O-Allyl-1,6-di-O-tert-butyldimethylsilyl-2,5-di-O-methanesulfonyl-D-mannitol (48) as Illustrated in FIG. 16

To a solution of 3,4-di-O-allyl-1,6-di-o-tert-butyldimethylsilyl-D-mannitol (vida supra; 9.79 g, 20.0 mmol) in 120 mL of freshly distilled dichloromethane was added triethylamine (11.20 mL, 80.4 mmol). The solution was cooled to 0° C. and methanesulfonyl chloride (4.90 mL, 60.1 mmol) was added slowly via a syringe. The reaction mixture was stirred at 0° C. for 65 minutes. Then 50 mL of ethyl ether was added to the reaction followed by addition of 200 mL distilled water. The above mixture was extracted with dichloromethane (60 mL×3). The organic layers were combined, dried over anhydrous Na$_2$SO$_4$, filtered and concentrated to give a yellow oil. The product was purified by chromatography using a gradient of ethyl acetate from 8% to 18% in hexanes. The purified product is colorless oil (12.52 g, yield 97%). R$_f$ 0.47 (EtOAc:hexanes=3:7, v/v). $^1$H NMR (400 MHz, CDCl$_3$) δ0.10 (12H, s), 0.91 (18H, s), 3.08 (6H, s), 3.86 (2H, d, J=3.2 Hz), 3.90 (2H, dd, J=11.8 Hz, J'=6.3 Hz), 4.18 (2H, tdd, J=1.2 Hz, J'=5.9 Hz, J''=12.1 Hz), 4.24 (2H, tdd, J=1.2 Hz, J'=5.7 Hz, J''=12.1 Hz), 4.80 (2H, m), 5.19 (2H, dd, J=10.4 Hz, J'=1.3 Hz), 5.29 (2H, ddd, J=1.4 Hz, J'=3.0 Hz, J''=17.2 Hz), 5.92 (2H, m) ppm. $^{13}$C NMR (CDCl$_3$) δ−5.4, 18.3, 25.8, 38.7, 61.8, 73.5, 77.9, 83.1, 117.7, 134.1 ppm. FAB-HRMS Calcd for C$_{26}$H$_{54}$O$_{10}$S$_2$Si$_2$CS: 779.1751. Found: [M+Cs]$^+$ 779.1728.

Synthesis of 3,4-di-O-Allyl-1,2:5,6-dianhydro-L-iditol (49) as Illustrated in FIG. 16

To a suspension of 3,4-di-O-allyl-1,6-di-O-tert-butyldimethylsilyl-2,5-di-O-methanesulfonyl-D-mannitol (48, 10.03 g, 15.5 mmol) in 140 mL of methanol was added (dropwise) concentrated HCl (aq, 5.14 mL) at 0° C. The solution was stirred at 0° C. for 60 minutes and another 2 hours at room temperature. The reaction was then re-cooled to 0° C. and 20% KOH (aq, 25.7 mL) was added. The reaction was stirred at 0° C. for 20 minutes and 3 hours at room temperature to become a white suspension. The reaction was then diluted with 100 mL of distilled water and was extracted with dichloromethane (120 mL×4). The organic layers were combined, dried over anhydrous $Na_2SO_4$, filtered and concentrated to give a yellow oil. The product was purified by chromatography using a gradient of ethyl acetate from 8% to 18% in hexanes. The purified product is light-yellowish oil (3.2 g, yield 90%). $R_f$ 0.35 (EtOAc:hexanes= 3:7, v/v). IR (film) υ 2993, 2870, 1646, 1459, 1421, 1255, 1123, 1086, 996, 925, 854, 834, 815 $cm^{-1}$. $^1H$ NMR (400 MHz, $CDCl_3$) δ2.65 (2H, dd, J=4.8 Hz, J'=2.2 Hz), 2.82 (2H, dd, J=4.8 Hz, J'=3.8 Hz), 4.09 (2H, tdd, J=1.4 Hz, J'=5.9 Hz, J"=12.9 Hz), 4.28 (2H, tdd, J=1.6 Hz, J'=5.3 Hz, J"=12.9 Hz), 5.18 (2H, ddd, J=1.3 Hz, J'=2.2 Hz, J"=10.4 Hz), 5.28 (2H, ddd, J=1.6 Hz, J'=3.3 Hz, J"=17.2 Hz), 5.90 (2H, m) ppm. $^{13}C$ NMR ($CDCl_3$) δ43.3, 52.1, 71.5, 80.5, 117.2, 134.4 ppm. FAB-HRMS Calcd for $C_{12}H_{18}O_4Na$: 249.1103. Found: [M+Na]$^+$ 249.1111. Anal. Calcd for $C_{12}H_{18}O_4$: C, 63.70; H, 8.02. Found, C, 63.49; H, 7.92.

General Procedure for Preparing 2,3,4,5-tetrahydroxyazepane derivatives and piperidine derivatives from bis-epoxides. Using the preparation of (3S,4R,5R,6S)-N-ally-4,5-di-O-allyl-3,4,5,6-tetrahydroxyazepane (50) and N-allyl-3,4-di-O-allyl-1-deoxynojirimycin (51) as an Example as Illustrated in FIG. 16

To a suspension of 3,4-di-O-allyl-1,2:5,6-dianhydro-L-iditol (49, 0.83 g, 3.67 mmol) in 15 mL of distilled water was added allylamine (3.34 mL, 44.1 mmol). The resulted suspension was cooled to 0° C. and was added perchloric acid (1.90 mL, 22.0 mmol) dropwise via a syringe. The reaction mixture was stirred at 0° C. for 2 hours and additional 20 hours at room temperature. 5 mL of saturated $NH_4Cl$ (aq) solution was added to the reaction, followed by addition of 15 mL distilled water. The aqueous solution was extracted with dichloromethane (25 mL×4). The organic layers were combined, dried over anhydrous $Na_2SO_4$, filtered, and concentrated to give a yellow oil as product. The products were further separated by column chromatography using a gradient of methanol from 0% to 4% in dichloromethane.

(3S,4R,5R,6S)-N-Ally-4,5-di-O-allyl-3,4,5,6-tetrahydroxyazepane (50) as Illustrated in FIG. 16

The major product (50) that was isolated was a light yellow oil at room temperature and was a off-white solid upon frozen (0.83 g, yield 80%). $R_f$ 0.37 (methanol:dichloromethane=5:95, v/v). IR (film) υ 3447, 2909, 2841, 1645, 1464, 1420, 1339, 1246, 1126, 1080, 1052, 995, 922, 832 $cm^{-1}$. $^1H$ NMR (400 MHz, $CDCl_3$) δ2.60 (2H, ddd, J=1.0 Hz, J'=8.2 Hz, J"=12.7 Hz), 2.86 (2H, ddd, J=1.1 Hz, J'=2.1 Hz, J"=12.6 Hz), 3.18 (2H, tdd, J=1.2 Hz, J'=6.7 Hz, J"=13.0 Hz), 3.23 (2H, tdd, J=1.3 Hz, J'=6.5 Hz, J"=13.0 Hz), 3.44 (2H, dd, J=4.2 Hz, J'=1.8 Hz), 3.56 (2H, s, broad), 3.73 (2H, m), 4.14 (2H, ddd, J=1.3 Hz, J'=5.8 Hz, J"=12.5 Hz), 4.24 (2H, ddd, J=1.4 Hz, J'=5.5 Hz, J"=12.5 Hz), 5.19 (4H, m), 5.29 (2H, ddd, J=1.6 Hz, J'=3.3 Hz, J"=17.2 Hz), 5.82 (1H, m), 5.93 (2H, m) ppm. $^{13}C$ NMR ($CDCl_3$) δ57.2, 62.3, 67.8, 72.5, 86.5, 117.2, 118.8, 134.5 ppm. FAB-HRMS Calcd for $C_{15}H_{25}NO_4Na$: 306.1681. Found: [M+Na]$^+$ 306.1687.

Anal. Calcd for $C_{15}H_{25}NO_4$: C, 63.58; H, 8.89; N, 4.94. Found, C, 63.56; H, 8.77; N, 5.03.

N-Allyl-3,4-di-O-allyl-1-deoxynojirimycin (51) as Illustrated in FIG. 16

The minor product (51) was isolated as a off-white solid (0.054 g, yield 5%). $R_f$ 0.05 (methanol:dichloromethane= 5:95, v/v). $^1H$ NMR (400 MHz, $CDCl_3$) δ2.25 (1H, dd, J=11.3 Hz, J'=10.1 Hz), 2.29 (1H, ddd, J=1.7 Hz, J'=3.0 Hz, J"=9.1 Hz), 3.06 (1H, dd, J=14.3 Hz, J'=7.7 Hz), 3.11 (1H, dd, J=11.3 Hz, J'4.6 Hz), 3.17 (1H, t, J=8.8 Hz), 3.39–3.45 (2H, m), 3.58 (1H, ddd, J=4.7 Hz, J'=8.8 Hz, J"=10.0 Hz), 3.71–3.77 (1H, m), 3.86 (1H, dd, J=11.8 Hz, H'=3.1 Hz), 4.11–4.27 (2H, m), 4.31–4.41 (2H, m), 5.16–5.25 (2H, m), 5.26–5.34 (2H, m), 5.84 (1H, m), 5.96 (2H, m) ppm. $^{13}C$ NMR ($CDCl_3$) δ55.3, 55.4, 57.4, 64.6, 69.2, 73.7, 73.9, 77.9, 86.4, 117.0, 117.2, 118.8, 133.4, 134.6, 134.9 ppm. FAB-HRMS Calcd for $C_{15}H_{25}NO_4Na$: 306.1681. Found: [M+Na]$^+$ 306.1690.

Synthesis of (3S,4R,5R,6S)-3,4,5,6-Tetrahydroxyazepane (6) as Illustrated in FIG. 16

Compound 50 (33.9 mg, 0.12 mmol) was dissolved in 2 mL of a methanol and water mixture (4:1, v/v). The resulting solution was degassed and was added 23 mg of 10% Pd/C and 55 μL of 2.3 M of perchloric acid solution (0.13 mmol). The reaction mixture was heated to reflux for 8 hours. The Pd/C was filtered and all solvents were evaporated. The crude product was then eluted from a Dowex ion-exchange [($NH_4$)$^+$ form, 200–400 mesh] column with gradient of ammonium hydroxide from 0 to 1M. The eluent was lyophilized to give a light yellow-colored solid (15.6 mg, yield 80%). $R_f$ 0.39 (ethyl alcohol:conc. $NH_4OH$=2:1, v/v). $^1H$ NMR (400 MHz, $D_2O$) δ2.80 (2H, dd, J=14.2 Hz, J'=7.6 Hz), 3.07 (2H, J=14.2 Hz, J'=4.0 Hz), 3.52 (2H, dd, J=5.6 Hz, J=2.2 Hz), 3.72 (2H, m) ppm. $^{13}C$ NMR ($D_2O$) δ53.0, 74.1, 80.0 ppm. FAB-HRMS Calcd for $C_6H_{14}NO_4$: 164.0923. Found: [M+H]$^+$ 164.0927.

Figure 17:
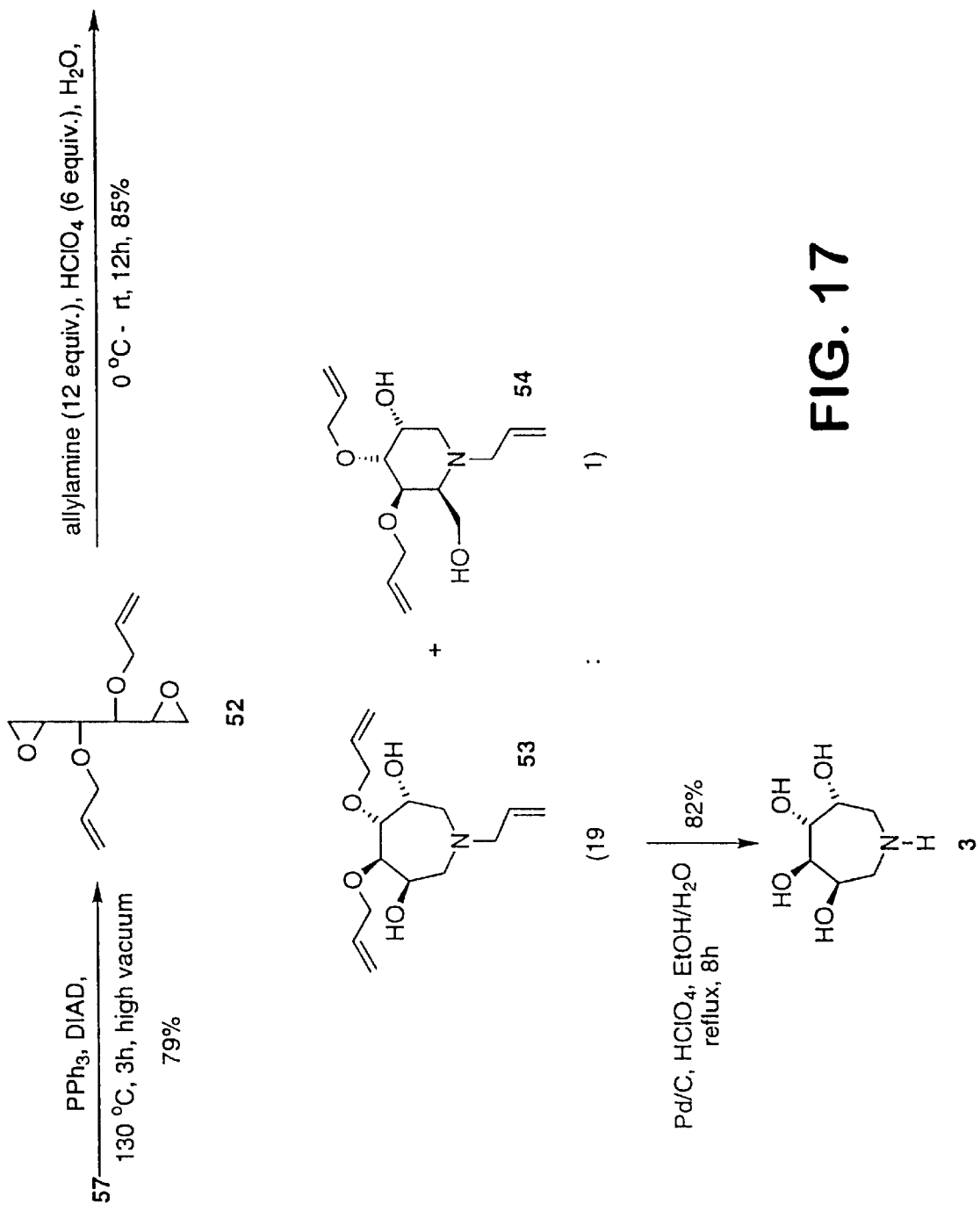
FIG. 17 illustrates the chemical synthesis of tetrahydroxy azepanes 3.

Synthesis of 1,2:5,6-Dianhydro-3,4-di-O-allyl-D-mannitol (52) as Illustrated in FIG. 17

3,4-di-O-Allyl-D-mannitol (57, 2.50 g, 9.5 mmol) and triphenylphosphine (5.75 g, 21.9 mmol) were suspended in 30 mL anhydrous benzene and was heated to reflux. Benzene was distilled until ca. 5 mL was left in the reaction container. The reaction mixture was cooled to room temperature and DIAD (5.07 mL, 23.9 mmol) was added. The reaction was stirred at room temperature for 30 minutes and then was heated to 130° C. under vacuum for 3 hours. The crude product was then purified with column chromatography to give a light yellow-colored oil as pure product (1.7 g, yield 79%). $R_f$ 0.36 (EtOAc:hexanes=3:7, v/v). $^1H$ NMR (400 MHz, $CDCl_3$) δ2.78 (2H, dd, J=5.3 Hz, J'=2.7 Hz), 2.86 (2H, dd, J=5.3 Hz, J'=3.8 Hz), 3.16 (2H, m), 3.37 (2H, dd, J=7.3 Hz, J'=2.6 Hz), 4.08 (2H, tdd, J=1.3 Hz, J'=6.1 Hz, J"=12.8 Hz), 4.21 (2H, tdd, J=1.4 Hz, J'=5.5,Hz, J"=12.8 Hz), 5.18 (2H, ddd, J=1.3 Hz, J'=2.8 Hz, J"=10.4 Hz), 5.26 (2H, ddd, J=1.6 Hz, J'=3.2 Hz, J"=17.2 Hz), 5.90 (2H, m) ppm. $^{13}C$ NMR ($CDCl_3$) δ46.3, 50.3, 72.4, 78.4, 117.4, 134.7 ppm. FAB-HRMS Calcd for $C_{12}H_{18}O_4Na$: 249.1103. Found: [M+Na]$^+$ 249.1113.

Synthesis of (3R,4R,5R,6R)-N-Ally-4,5-di-O-allyl-3,4,5,6-tetrahydroxyazepane (13) as illustrated in FIG. 17

The procedure for preparing compound 53 was the same as that for compound 50, except the bis-epoxide used was 1,2:5,6-dianhydro-3,4-di-o-allyl-D-mannitol (52). Yield 81%. $R_f$ 0.41 (methanol:dichloromethane=1:9, v/v). IR (film) υ 3419, 2912, 2862, 1645, 1462, 1420, 1339, 1267, 1225, 1080, 996, 921, 867, 831 $cm^{-1}$. $^1H$ NMR (400 MHz, $CDCl_3$) δ2.70 (2H, ddd, J=0.8 Hz, J'=6.3 Hz, J"=13.2 Hz), 2.82 (2H, ddd, J=0.8 Hz, J'=3.6 Hz, J"=13.2 Hz), 3.17 (2H, td, J=1.2 Hz, J'=6.5 Hz), 3.68 (2H, dd, J=1.3 Hz, J'=1.6 Hz), 4.06 (2H, m), 4.13 (2H, tdd, J=1.4 Hz, J'=5.9 Hz, J"=12.7 Hz), 4.23 (2H, tdd, J=1.5 Hz, J'=5.4 Hz, J"=12.7 Hz), 5.17 (4H, m), 5.29 (2H, ddd, J=1.6 Hz, J'=3.3 Hz, J"=17.2 Hz), 5.84 (1H, m), 5.94 (2H, m) ppm. $^{13}$C NMR (CDCl$_3$) δ57.0, 62.4, 68.9, 72.3, 80.6, 117.0, 118.1, 118.3, 135.0 ppm. FAB-HRMS Calcd for $C_{15}H_{26}NO_4$: 284.1862. Found: [M+H]$^+$ 284.1855.

Synthesis of N-Allyl-3,4-di-O-allyl-L-gulo-piperidine (54) as Illustrated in FIG. 17

Compound 54 was isolated as a light yellow oil. Yield 4%. R$_f$ 0.45 (methanol:dichloromethane=1:9, v/v). IR (film) υ 3402, 3073, 2917, 2854, 2360, 1640, 1452, 1420, 1342, 1259, 1134, 1072, 993, 921, 669 cm$^{-1}$. $^1$H NMR (400 MHz, CDCl$_3$) δ2.41 (1H, s, broad), 2.69 (1H, dd, J=12.8 Hz, J'=6.2 Hz), 2.80 (1H, dd, J=12.8 Hz, J'=3.3 Hz), 2.99 (1H, dd, J=10.1 Hz, J'=5.2 Hz), 3.41 (2H, dd, J=6.5 Hz, J'=0.9 Hz), 3.59 (1H, dd, J=14.1 Hz, J'=3.5 Hz), 3.70 (1H, dd, J=11.4 Hz, J'=5.5 Hz), 3.85–3.90 (2H, m), 4.02 (1H, m), 4.06–4.22 (4H, m), 5.15–5.23 (4H, m), 5.26–5.33 (2H, m), 5.80–5.97 (3H, m) ppm. $^{13}$C NMR (CDCl$_3$) δ50.7, 57.6, 58.8, 58.9, 67.3, 71.5, 72.1, 76.4, 76.8, 117.4, 117.9, 118.1, 134.5, 134.6, 135.1 ppm. FAB-HRMS Calcd for $C_{15}H_{25}NO_4Na$: 306.1681. Found: [M+H]$^+$ 306.1689.

Synthesis of (3R,4R,5R,6R)-3,4,5,6-Tetrahydroxyazepane (3) as Illustrated in FIG. 17

The procedure for preparing compound 3 is the same as that of compound 6, except the azepane 53 was used as starting material. Compound 3 was obtained as a off-white solid. Yield 80%. R$_f$ 0.34 (ethyl alcohol:conc. NH$_4$OH=2:1, v/v). $^1$H NMR (400 MHz, D$_2$O) δ2.79 (2H, dd, J=14.4 Hz, J'=6.4 Hz), 2.85 (2H, dd, J=14.4 Hz, J'=3.5 Hz), 3.75 (2H, s), 3.95 (2H, m) ppm. $^{13}$C NMR (D$_2$O) δ47.5, 69.4, 75.6 ppm. FAB-HRMS Calcd for $C_6H_{14}NO_4$: 164.0923. Found: [M+H]$^+$ 164.0925.

Figure 18:
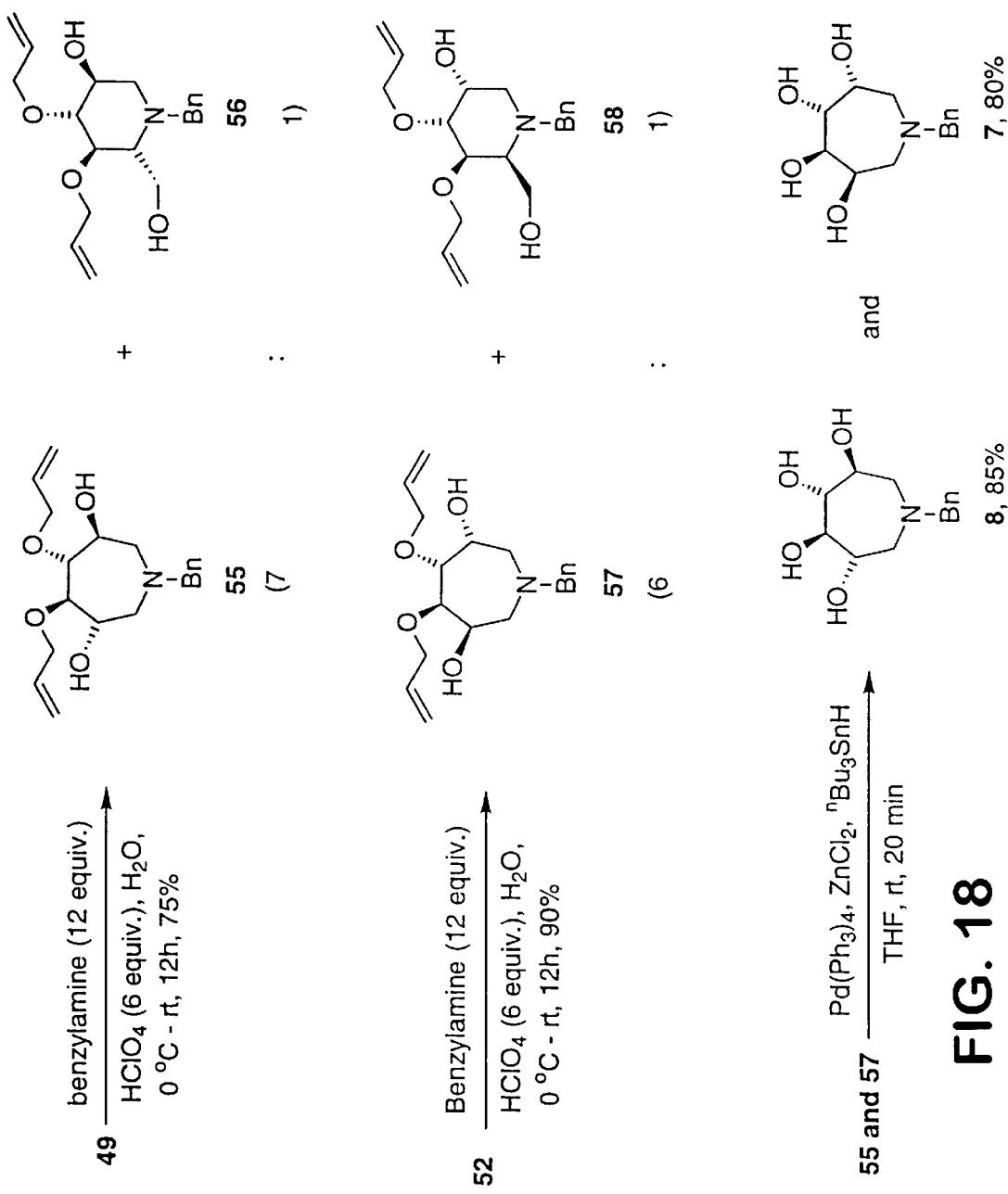
FIG. 18 illustrates the chemical synthesis of tetrahydroxy azepanes 55, 56, 57, 58, 7 and 8.

Synthesis of (3S,4R,5R,6S)-N-Benzyl-4,5-di-O-allyl-3,4,5,6-tetrahydroxyazepane (5S) as Illustrated in FIG. 18

The procedure for preparing compound 55 is the same as that for compound 50, except benzylamine was used here in place of allylamine. Compound 55 was obtained as a yellow oil after purification. Yield 66%. R$_f$ 0.59 (methanol:dichloromethane 5:95, v/v). $^1$H NMR (400 MHz, CDCl$_3$) δ2.61 (2H, dd, J=0.8 Hz, J'=8.2 Hz, J"=12.6 Hz), 2.88 (2H, ddd, J=1.0 Hz, J'=1.9 Hz, J"=12.6 Hz), 3.44 (2H, dd, J=4.2 Hz, J'1.8 Hz), 3.55 (2H, s, broad), 3.69 (1H, d, J=13.1 Hz), 3.74 (1H, d, J=13.1 Hz), 4.13 (2H, tdd, J=1.3 Hz, J'=5.8 Hz, J"=12.5 Hz), 4.23 (2H, tdd, J=1.4 Hz, J'=5.5 Hz, J"=12.6 Hz), 5.18 (2H, ddd, J=1.3 Hz, J'=2.6 Hz, J"=10.4 Hz), 5.28 (2H, ddd, J=1.6 Hz, J'=3.2 Hz, J"=17.2 Hz), 5.92 (2H, m), 7.25–7.35 (5H, m) ppm. $^{13}$C NMR (CDCl$_3$) δ57.3, 63.5, 67.8, 72.5, 86.4, 117.2, 127.6, 128.5, 129.1, 134.5, 137.6 ppm. FAB-HRMS Calcd for $C_{19}H_{28}NO_4$: 334.2018. Found: [M+H]$^+$ 334.2011.

Synthesis of N-Benzyl-3,4-di-O-allyl-1-deoxynojirimycin (56) as Illustrated in FIG. 18

Compound 56 was obtained as a yellow oil after purification. Yield 9%. R$_f$ 0.34 (methanol:dichloromethane=5:95, v/v). $^1$H NMR (400 MHz, CDCl$_3$) δ2.13 (1H, dd, J=11.3 Hz, J'=9.8 Hz), 2.37 (1H, dd, broad, J=7.5 Hz), 2.36 (2H, m), 3.05 (1H, dd, J=11.3 Hz, J'=4.4 Hz), 3.21 (1H, t, J=8.6 Hz), 3.33 (1H, d, J=13.5), 3.50 (1H, d, J=8.7 Hz), 3.54 (1H, m), 3.81 (1H, dd, broad, J=11.5 Hz, J'=6.2 Hz), 4.00 (1H, dd, J=11.9 Hz, J'=3.1 Hz), 4.07 (1H, d, J=13.5 Hz), 4.20 (2H, m), 4.35 (2H, m), 5.19 (2H, m), 5.30 (2H, m), 5.96 (2H, m) 7.24 –7.35 (5H, m) ppm. $^{13}$C NMR (CDCl$_3$) δ55.1, 57.0, 57.8, 65.5, 69.0, 73.6, 73.8, 78.0, 85.8, 117.1, 117.2, 127.4, 128.5, 128.8, 134.6, 134.9, 137.7 ppm. FAB-HRMS Calcd for $C_{19}H_{28}NO_4$: 334.2018. Found: [M+H]$^+$ 334.2027.

Synthesis of (3R,4R,5R,6R)-N-Benzyl-4,5-di-O-allyl-3,4,5,6-tetrahydroxyazepane (57) as Illustrated in FIG. 18

The procedure for preparing compound 57 was the same as that for compound 50, except the bis-epoxide used was 1,2:5,6-dianhydro-3,4-di-O-allyl-D-mannitol (52) and the amine used was benzylamine. Compound 57 was isolated as a yellow oil. Yield 78%. R$_f$ 0.29 (methanol:dichloromethane=5:95, v/v). $^1$H NMR (400 MHz, CDCl$_3$) δ2.73 (2H, dd, J=12.9 Hz, J'=6.4 Hz), 2.83 (2H, dd, J=13.2 Hz, J'=3.4 Hz), 3.29 (2H, s), 3.70 (4H, m), 4.05 (2H, m), 4.12 (2H, tdd, J=1.4 Hz, J'=5.8 Hz, J"=12.7 Hz), 4.22 (2H, tdd, J=1.5 Hz, J'=5.4 Hz, J"=12.7 Hz), 5.17 (2H, ddd, J=1.3 Hz, J'=2.9 Hz, J"=10.4 Hz), 5.29 (2H, ddd, J=1.6 Hz, J'=3.3 Hz, J"=17.2 Hz), 5.93 (2H, m), 7.24–7.35 (5H, m) ppm. $^{13}$C NMR (CDCl$_3$) δ57.2, 63.6, 68.8, 72.2, 80.8, 117.0, 127.4, 128.5, 128.9, 134.9, 138.3 ppm. FAB-HRMS Calcd for $C_{19}H_{28}NO_4$: 334.2018. Found: [M+H]$^+$ 334.2028.

Synthesis of N-Benzyl-3,4-di-O-allyl-L-gulo-piperidine (58) as Illustrated in FIG. 18

Compound 58 was isolated as a yellow oil. Yield 12%. R$_f$ 0.50 (methanol:dichloromethane=5:95, v/v). $^1$H NMR (400 MHz, CDCl$_3$) δ2.46 (1H, s, broad), 2.71 (1H, dd, J=13.8 Hz, J'=4.5 Hz), 2.79 (1H, dd, J=13.6 Hz, J'=2.8 Hz), 3.10 (1H, dd, J=11.6 Hz, J'=6.0 Hz), 3.56 (1H, dd, J=8.1 Hz, J'=3.5 Hz), 3.69 (1H, dd, J=11.2 Hz, J'=6.8 Hz), 3.85–4.00 (5H, m), 4.07–4.22 (4H, m), 5.20 (2H, m), 5.30 (2H, m), 5.92 (2H, m), 7.23–7.38 (5H, m) ppm. $^{13}$C NMR (CDCl$_3$) δ49.4, 58.1, 59.2, 59.8, 67.9, 71.4, 72.2, 75.6, 77.6, 117.2, 117.4, 127.2, 128.4, 129.0, 134.6, 134.7, 139.1 ppm. FAB-HRMS Calcd for $C_{19}H_{28}NO_4$: 334.2018. Found: [M+H]$^+$ 334.2026.

Synthesis of (3S,4R,5R,6S)-N-Benzyl-3,4,5,6-tetrahydroxyazepane (8) as Illustrated in FIG. 18

To a solution of compound 55 (18.9 mg, 0.06 mmol) in anhydrous THF, anhydrous zinc chloride (39 mg, 0.29 mmol) was added. The resulting white suspension was stirred at room temperature for 10 minutes and then tetrakis(triphenylphosphin)palladium (0) (16.4 mg, 0.014 mmol) was added. The resulting light yellow suspension was stirred at room temperature for 10 minutes and tributyltin hydride (63 mL, 0.23 mmol) was added via a syringe. The reaction mixture was stirred at room temperature for 30 minutes. All volatiles were removed and 1.0 mL of 1 N HCl (aq) solution was added to the residue and was then evaporated. Another 1 mL of saturated NaHCO$_3$ (aq) was added to the resulted yellow residue and was evaporated to dryness. The white solid was extracted with methanol (6 mL×4). The organic solvent was evaporated and the crude product was purified by preparative tlc (methanol:ethyl acetate=1:9, v/v). The isolated product was a light yellow oil (12.2 mg, yield 85%). R$_f$ 0.30 (methanol:ethyl acetate=1:9, v/v). $^1$H NMR (400 MHz, CD$_3$OD) δ2.54 (2H, dd, J=12.9 Hz, J'=8.0 Hz), 2.82 (2H, dd, J=13.0 Hz, J'=4.5 Hz), 3.42 (2H, dd, J=5.6 Hz, J'=2.3 Hz), 3.55 (2H, m), 3.62 (1H, d, J=13.2 Hz), 3.70 (1H, d, J=13.2 Hz), 7.21–7.36 (5H, m) ppm. $^{13}$C NMR (CD$_3$OD) δ60.2, 64.5, 73.3, 77.6, 128.3, 129.4, 130.1, 140.1 ppm. FAB-HRMS Calcd for C$_{13}$H$_{20}$NO$_4$: 254.1392. Found: [M+H]$^+$ 254.1397.

Synthesis of (3R,4R,5R,6R)-N-Benzyl-3,4,5,6-tetrahydroxyazepane (7) as Illustrated in FIG. 18

The procedure for preparing compound 7 was the same as that for compound 8, except the starting material used was 57 instead of 55. Compound 7 was isolated as a light yellow oil. Yield 80%. R$_f$ 0.31 (methanol:ethyl acetate=1:9, v/v). $^1$H NMR (400 MHz, CD$_3$OD) δ2.70 (2H, dd, J=13.0 Hz, J'=7.2 Hz), 2.81 (2H, dd, J=13.0 Hz, J'=4.6 Hz), 3.62 (1H, d, J=13.0 Hz), 3.70 (1H, d, J=13.0 Hz), 3.88 (2H, s, broad), 3.99 (2H, m), 7.22–7.37 (5H, m) ppm. $^{13}$C NMR (CD$_3$OD) δ58.1, 64.4, 70.2, 74.5, 128.4, 129.5, 130.2, 140.0 ppm. FAB-HRMS Calcd for C$_{13}$H$_{20}$NO$_4$: 254.1392. Found: [M+H]$^+$ 254.1398. An x-ray crystal structure was obtained. Compound 7 was crystallized from water and was a colorless, plate like crystal. The crystal was mounted alongwith the largest dimension and data were collected with a Rigaku AFC6R diffratometer equipped with a copper rotating anode and a highly oriented graphite monochromator. A constant scan speed of 8°/minute in ω was used and the weak reflections [I<5σ(I)] were rescanned to a maximum of 6 times and the counts accumulated to assure good counting statistics. The intensities of three monitor reflections measured after every 200 reflections did not change significantly during 13 hrs of x-ray exposure. Unit cell dimensions and standard deviations were obtained by least squares fit to 25 reflections (50<2θ<80°). The data were corrected for Lorentz and polarization effects and not for absorption because of low value of μ. The system absences (0k0, k=2n+1) indicated a choice between the space groups P2$_1$ and P2$_1$/m. Since the compound is enantiomeric, the former space group was used. The structure was solved by direct methods using SHELX86. All non-hydrogen atoms were refined anisotropically by the full matrix least-squares method. Unit cell dimesions are: a=6.279 (1) Å, b=9.604 (2) Å, c=10.310 (1) Å; α=90°, β=92.86 (1)°, γ=90°. Two molecules were found in the unit cell. They were linked via an intermolecular hydrogen bond, the bond length of H(3A)-O4' is 1.938 Å.

Figure 19:
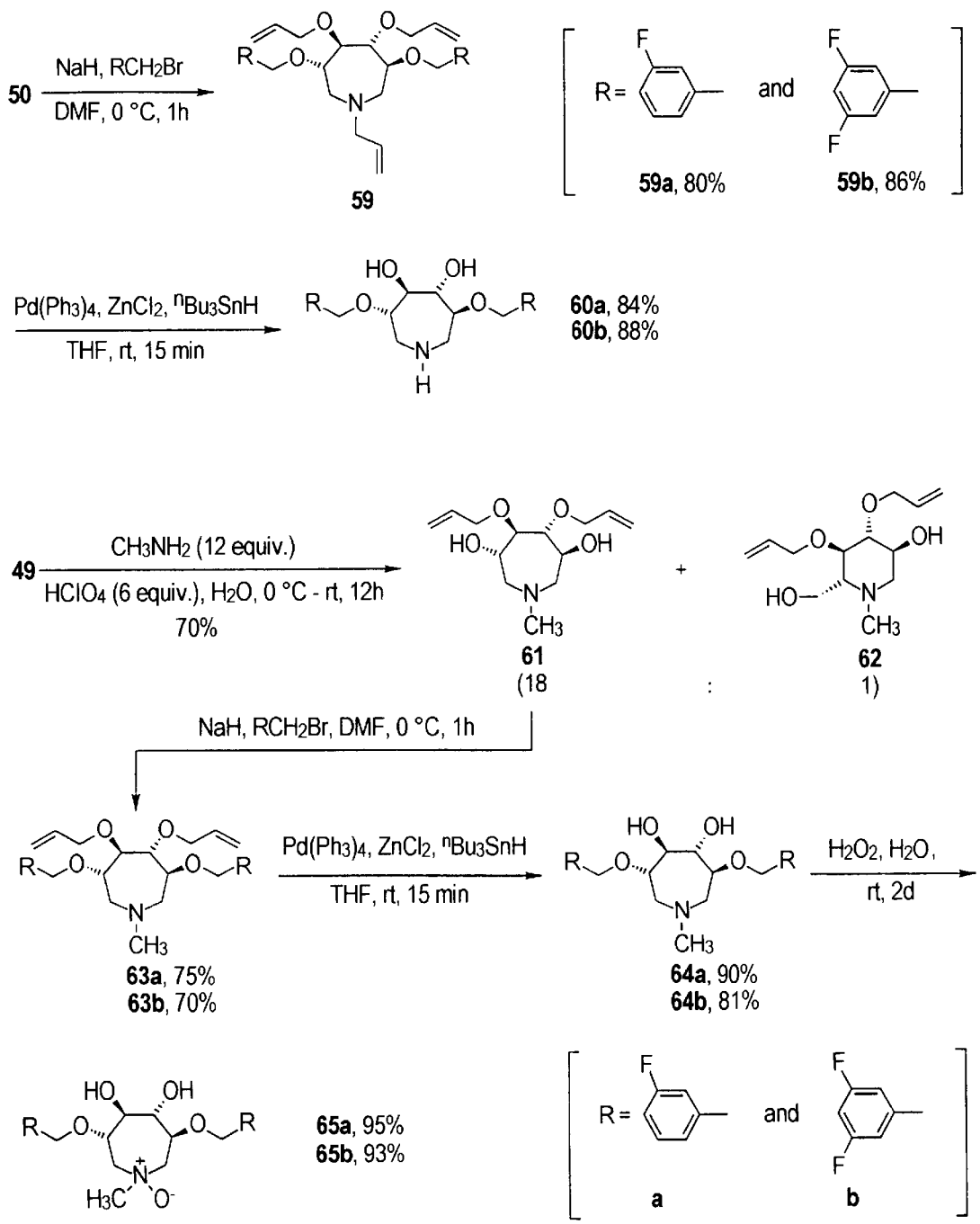
FIG. 19 illustrates the chemical synthesis of tetrahydroxy azepanes, 63a, 63b; 64a, 64b, 65a, and 65b.

Synthesis of (3S,4R,5R,6S)-N-Allyl-4,5-di-O-allyl-3,6-di-O-(3'-fluorobenzyl)-3,4,5,6-tetrahydroxyazepane (59a) as Illustrated in FIG. 19

Compound 50 (98.5 mg, 0.35 mmol) and tetrabutylammonium iodide (6.4 mg, 0.017 mmol) were dissolved in anhydrous 8 mL DMF and the resulting solution was cooled to 0° C. Sodium hydride powder (21 mg, 0.88 mmol) was added to the above solution to form a suspension which was stirred at 0° C. for 20 minutes, 30 minutes at room temperature and was re-cooled to 0° C. 3-Fluorobenzyl bromide (94 μL, 0.76 mmol) was added to the above suspension, the reaction mixture was then allowed to stir at 0° C. for 40 minutes. The reaction was quenched with 20 mL of water followed by extraction with dichloromethane (20 mL×4). The combined organic phases was dried (over anhydrous MgSO$_4$), filtered and concentrated. The crude product was purified with column chromatography with a gradient of 5% to 13% of ethyl acetate in hexanes (v/v). The product was obtained as a yellow oil (139 mg, yield 80%). R$_f$ 0.38 (ethyl acetate:hexanes=3:7, v/v). IR (film) υ 3076, 2852, 1617, 1591, 1488, 1450, 1346, 1255, 1137, 1088, 994, 923, 781, 747, 684 cm$^{-1}$. $^1$H NMR (400 MHz, CDCl$_3$) δ2.67 (2H, dd, J=13.3 Hz, J'=7.2 Hz), 2.76 (2H, dd, J=13.3 Hz, J'=3.0 Hz), 3.14 (2H, d, broad, J=6.4 Hz), 3.59 (2H, dd, J=5.83 Hz, J'=1.8 Hz), 3.70 (2H, m), 4.15 (2H, tdd, J=1.4 Hz, J'=5.6 Hz, J"=12.5 Hz), 4.26 (2H, tdd, J=1.5 Hz, J'=5.4 Hz, J"=12.5 Hz), 4.61 (2H, d, J=12.1 Hz), 4.68 (2H, d, J=12.1 Hz), 5.14–5.19 (4H, m), 5.28 (2H, ddd, J=1.6 Hz, J'=3.4 Hz, J"=17.2 Hz), 5.86 (1H, m), 5.94 (2H, m), 6.96 (2H, m), 7.10 (4H, m), 7.25–7.30 (2H, m) ppm. $^{13}$C NMR (CDCl$_3$) δ55.1, 62.1, 71.6, 72.9, 79.9, 83.2, 114.2, 114.3, 114.4, 114.5, 116.6, 117.9, 123.0, 129.7, 129.8, 135.2, 135.6, 141.4, 141.5 ppm. FAB-HRMS Calcd for C$_{29}$H$_{35}$F$_2$NO$_4$Cs: 632.1588. Found: [M+Cs]$^+$ 632.1568.

Synthesis of (3S,4R,5R,6S)-N-Allyl-4,5-di-O-allyl-3,6-di-O-(3',5'-difluorobenzyl)-3,4,5,6-tetrahydroxyazepane (59b) as Illustrated in FIG. 19

The procedure for preparing 59b was the same as that for 59a, except 3,5-difluorotoluene was used in place of 3-fluorobenzyl bromide. Yield 86%. R$_f$ 0.51 (ethyl acetate:hexanes=3:7, v/v). $^1$H NMR (400 MHz, CDCl$_3$) δ2.68 (2H, dd, J=13.4 Hz, J'=7.1 Hz), 2.76 (2H, dd, J=13.4 Hz, J'3.0 Hz), 3.15 (2H, dd, J=6.5 Hz, J'=1.1 Hz), 3.59 (2H, dd, J=5.9 Hz, J'=1.8 Hz), 3.69 (2H, m), 4.14 (2H, tdd, J=1.4 Hz, J'=5.7 Hz, J"=12.5 Hz), 4.27 (2H, tdd, J=1.5 Hz, J'=5.4 Hz, J"=12.5 Hz), 4.59 (2H, d, J=12.6 Hz), 4.65 (2H, d, J=12.6 Hz), 5.15–5.20 (4H, m), 5.28 (2H, ddd, J=1.7 Hz, J'=3.4 Hz, J"=17.2 Hz), 5.85 (1H, m), 5.93 (2H, m), 6.70 (2H, m), 6.89 (4H, m) ppm. $^{13}$C NMR (CDCl$_3$) δ54.9, 62.1, 71.1, 72.9, 80.2, 83.0, 102.4, 102.6, 102.9, 109.8, 109.9, 110.0, 110.1, 116.7, 118.1, 135.0, 135.6, 142.9, 143.0 ppm. FAB-HRMS Calcd for C$_{29}$H$_{33}$F$_4$NO$_4$Cs: 668.1400. Found: [M+Cs]$^+$ 668.1420.

Synthesis of (3S,4R,5R,6S)-3,6-di-O-(3'-fluorobenzyl)-3,4,5,6-tetrahydroxyazepane (60a) as Illustrated in FIG. 19

To a solution of compound 60a (11.6 mg, 0.02 mmol) in 5 mL of anhydrous THF was added anhydrous zinc chloride (9.5 mg, 0.07 mmol). After 10 minutes of stirring at room temperature, tetrakis(triphenylphosphine)palladium (0) (7 mg, 0.006 mmol) was added. The reaction mixture was stirred for 15 minutes and tributyltin hydride (26 μL, 0.09 mmol) was added. The reaction was stirred for 15 minutes and organic solvent was removed, followed by addition of 1 mL of water and 1 mL of 1 N HCl (aq). All volatiles were removed and 2 mL of saturated NaHCO$_3$ (aq) was added and then evaporated to give a white solid which was extracted with methanol, filtered, and evaporated. The crude product was purified with preparative tlc (500 μm, developed in 1:9=methanol:dichloromethane, v/v). The isolated product was a yellow oil weighed 7.4 mg. Yield 84%. R$_f$ 0.29 (methanol:dichloromethane=1:9, v/v). $^1$H NMR (400 MHz, CDCl$_3$) δ2.91 (2H, dd, J=14.1 Hz, J'=6.5 Hz), 3.08 (2H, dd, J=14.1 Hz, J'=4.1 Hz), 3.27 (2H, s, broad), 3.47 (2H, m), 3.79 (2H, dd, J=4.5 Hz, J'=2.1 Hz), 4.65 (4H, s), 6.98 (2H, m), 7.09 (4H, m), 7.31 (2H, m) ppm. $^{13}$C NMR (CDCl$_3$) δ50.8, 71.4, 75.3, 81.6, 114.4, 114.6, 114.7, 114.8, 123.1, 130.0, 140.6, 140.7, 161.7, 164.1 ppm. FAB-HRMS Calcd for C$_{20}$H$_{24}$F$_2$NO$_4$: 380.1673. Found: [M+H]$^+$ 380.1685.

Synthesis of (3S,4R,5R,6S)-3,6-di-O-(3',5'-difluorobenzyl)-3,4,5,6-tetrahydroxyazepane (60b) as Illustrated in FIG. 19

Compound 20b was prepared analogosly to compound 60a, using the starting material 59b. Compound 60b was isolated as a yellow oil. Yield 88%. R$_f$ 0.50

(methanol:dichloromethane=1:9, v/v). $^1$H NMR (400 MHz, CDCl$_3$) δ2.92 (2H, dd, J=14.1 Hz, J'=6.5 Hz), 3.09 (2H, dd, J=14.1 Hz, J'=4.2 Hz), 3.23 (2H, s broad), 3.46 (2H, m), 3.79 (2H, dd, J=4.6 Hz, J'=2.1 Hz), 4.65 (4H, s), 6.73 (2H, m), 6.88 (4H, m) ppm. $^{13}$C NMR (CDCl$_3$) δ51.2, 70.9, 75.1, 82.0, 102.8, 103.0, 103.3, 109.9, 110.0, 110.1, 110.2, 142.1, 142.2, 161.9, 164.2 ppm. FAB-HRMS Calcd for C$_{20}$H$_{22}$F4NO$_4$: 416.1485. Found: [M+H]$^+$ 416.1502.

Synthesis of (3S,4R,5R,6S)-4,5-di-O-Allyl-N-methyl-3,4,5,6-tetrahydroxyazepane (61) as Illustrated in FIG. 19

Compound 61 was prepared analogously to compound 50, using methylamine in place of allylamine. Compound 61 was isolated as a light yellow oil. Yield 66.5%. R$_f$ 0.44 (methanol:dichloromethane=2:8, v/v). IR (film) υ 3427, 3079, 2943, 2902, 2857, 2810, 1646, 1464, 1424, 1333, 1245, 1164, 1127, 1080, 1034, 996, 924, 834 cm$^1$. $^1$H NMR (400 MHz, CDCl$_3$) δ2.45 (3H, s), 2.51 (2H, dd, J=12.3 Hz, J'=8.5 Hz), 2.82 (2H, d, broad, J=12.6 Hz), 3.43 (2H, dd, J=4.2 Hz, J'=1.7 Hz), 3.74 (2H, m), 4.14 (2H, tdd, J=1.3 Hz, J'=5.7 Hz, J''=12.5 Hz), 4.24 (2H, tdd, J=1.4 Hz, J'=5.5 Hz, J''=12.5 Hz), 5.19 (2H, m), 5.29 (2H, ddd, J=1.6 Hz, J'=3.2 Hz, J''=17.2 Hz), 5.93 (2H, m) ppm. $^{13}$C NMR (CDCl$_3$) δ47.8, 59.8, 67.6, 72.5, 86.3, 117.3, 134.5 ppm. FAB-HRMS Calcd for C$_{13}$H$_{24}$NO$_4$: 258.1705. Found: [M+H]$^+$ 258.1695.

Synthesis of 3,4-di-O-Allyl-N-methyl-1-deoxynojirimycin (62) as Illustrated in FIG. 19

Compound 62 was separated from 61 as a minor product. Yield 3.5%. R$_f$ 0.44 (methanol:dichloromethane=2:8, v/v). $^1$H NMR (400 MHz, CDCl$_3$) δ1.98 (1H, d, broad, J=9.4 Hz), 2.21 (1H, t, J=10.6 Hz), 2.35 (3H, s), 2.92 (1H, d, broad, J=13.2 Hz), 3.05 (1H, dd, J=10.9 Hz, J'=3.9 Hz), 3.17 (1H, t, J=9.1 Hz), 3.44 (1H, t, J=9.3 Hz), 3.48 (1H, s, broad), 3.63 (1H, m), 3.76 (1H, dd, J=11.8 Hz, J'=1.0 Hz), 3.83 (1H, dd, J=11.8 Hz, J'=2.7 Hz), 4.19 (2H, m), 4.37 (2H, m), 5.19 (2H, m), 5.31 (2H, m), 5.95 (2H, m) ppm. $^{13}$C NMR (CDCl$_3$) δ41.7, 57.5, 59.5, 67.8, 69.0, 72.3, 73.9, 77.6, 86.7, 117.1, 117.4, 134.6, 134.9 ppm. FAB-HRMS Calcd for C$_{13}$H$_{24}$NO$_4$: 258.1705. Found: [M+H]$^+$ 258.1708.

Synthesis of (3S,4R,5R,6S)-4,5-di-O-Allyl-3,6-di-O-(3'-fluorobenzyl)-N-methyl-3,4,5,6-tetrahydroxyazepane (63a) as Illustrated in FIG. 19

Compound 63a was prepared analogously to 59a, using the starting material 61. Compound 63a was isolated as a colorless oil. Yield 75%. R$_f$ 0.41 (methanol:dichloromethane=5:95, v/v). IR (film) υ 2856, 1617, 1591, 1488, 1449, 1348, 1254, 1137, 1085, 923, 862, 780, 747, 683 cm$^{-1}$. $^1$H NMR (400 MHz, CDCl$_3$) δ2.39 (3H, s), 2.64 (2H, dd, J=13.2 Hz, J'=7.0 Hz), 2.70 (2H, dd, J=13.2 Hz, J'=3.0 Hz), 3.61 (2H, dd, J=8.3 Hz, J'=2.1 Hz), 3.75 (2H, m), 4.13 (2H, tdd, J=1.4 Hz, J'=5.6 Hz, J'=12.6 Hz), 4.24 (2H, tdd, J=1.5 Hz, J'=5.4 Hz, J''=12.6 Hz), 4.62 (2H, d,J=12.2 Hz), 4.70 (2H, d,J=12.2 Hz), 5.16 (2H, ddd, J=1.3 Hz, J'=3.0 Hz, J''=10.4 Hz), 5.28 (2H, ddd, J=1.6 Hz, J'=3.4 Hz, J''=17.2 Hz), 6.96 (2H, m), 7.11 (4H, m), 7.23–7.25 (2H, m) ppm. $^{13}$C NMR (CDCl$_3$) δ47.7, 57.3, 71.6, 79.0, 82.2, 114.2, 114.4, 114.5, 114.6, 116.8, 129.7, 129.8, 134.9 ppm. FAB-HRMS Calcd for C$_{27}$H$_{34}$F$_2$NO$_4$: 474.2456. Found: [M+H]$^+$ 474.2469.

Synthesis of (3S,4R,5R,6S)-4,5-di-O-Allyl-3,6-di-O-(3',5'-difluorobenzyl)-N-methyl-3,4,5,6-tetrahydroxy-azepane (63b) as Illustrated in FIG. 19

Compound 63b was prepared analogously to 19b, using the starting material 61. Compound 63b was isolated as a colorless oil. Yield 75%. R$_f$ 0.33 (methanol:dichloromethane=1:9, v/v). IR (film) υ 2846, 1625, 1597, 1459, 1321, 1117, 1082, 986, 923, 874, 848, 770, 669 cm$^{-1}$. $^1$H NMR (400 MHz, CDCl$_3$) δ2.40 (3H, s), 2.68 (4H, m), 3.62 (2H, m), 3.76 (2H, m), 4.11 (2H, tdd, J=1.4 Hz, J'=5.7 Hz, J''=12.6 Hz), 4.25 (2H, tdd, J=1.5 Hz, J'=5.3 Hz, J''=12.6 Hz), 4.61 (2H, d, J=12.6 Hz), 4.66 (2H, d, J=12.6 Hz), 5.18 (2H, ddd, J=1.3 Hz, J'=2.9 Hz, J''=10.4 Hz), 5.28 (2H, ddd, J=1.7 Hz, J'=3.3 Hz, J'=17.2 Hz), 5.92 (2H, m), 6.70 (2H, m), 6.90 (4H, m) ppm. $^{13}$C NMR (CDCl$_3$) δ47.8, 57.3, 71.0, 72.4, 79.8, 82.4, 102.4, 102.7, 102.9, 109.8, 109.9, 110.0, 110.1, 116.8, 134.8 ppm. FAB-HRMS Calcd for C$_{27}$H$_{32}$F$_4$NO$_4$: 510.2267. Found: [M+H]$^+$ 510.2253.

Synthesis of (3S,4R,5R,6S)-3,6-di-O-(3'-Fluorobenzyl)-N-methyl-3,4,5,6-tetrahydroxyazepane (64a) as Illustrated in FIG. 19

Compound 64a was prepared in a similar fashion as 60a, except the starting material used was 63a. Compound 64a was isolated as a yellow oil. Yield 90%. R$_f$ 0.45 (methanol:dichloromethane=1:9, v/v). $^1$H NMR (400 MHz, CDCl$_3$) δ2.39 (3H, s), 2.59 (2H, ddd, J=0.6 Hz, J'=6.9 Hz, J''=13.4 Hz), 2.84 (2H, dd, J=13.4 Hz, J'=4.6 Hz), 3.35 (2H, s), 3.56 (2H, m), 3.77 (2H, m), 4.66 (4H, s), 6.98 (2H, m), 7.10 (4H, m), 7.30 (2H, m) ppm. $^{13}$C NMR (CDCl$_3$) δ48.3, 59.7, 71.5, 75.0, 80.2, 114.4, 114.5, 114.6, 114.7, 123.1, 129.9, 130.0 ppm. FAB-HRMS Calcd for C$_{21}$H$_{26}$F$_2$NO$_4$: 394.1830. Found: (M+H]$^+$394.1842.

Synthesis of (3S,4R,5R,6S)-3,6-di-O-(3',5'-difluorobenzyl)-N-methyl-3,4,5,6-tetrahydroxyazepane (64b) as Illustrated in FIG. 19

Compound 64d was prepared in a similar fashion as 60b, except the starting material used was 63b. Compound 64b was isolated as a light yellowish oil. Yield 81%. R$_f$ 0.37 (methanol:chloroform=0.5:9.5, v/v). IR (film) υ 3456, 3412, 2888, 2810, 1627, 1596, 1460, 1364, 1320, 1117, 984, 963, 850, 668 cm$^{-1}$. $^1$H NMR (400 MHz, CDCl$_3$) δ2.41 (3H, s), 2.60 (2H, dd, J=13.3 Hz, J'=6.9 Hz), 2.85 (2H, dd, J=13.3 Hz, J'=4.5 Hz), 3.32 (2H, s, broad), 3.55 (2H, m), 3.78 (2H, dd, J=5.1 Hz, J'=2.2 Hz), 4.63 (2H, d, J=12.6 Hz), 4.65 (2H, d, J=12.6 Hz), 6.72 (2H, m), 6.88 (4H, m) ppm. $^{13}$C NMR (CDCl$_3$) δ48.3, 59.8, 71.0, 74.9, 80.6, 102.7, 103.0, 103.2, 109.9, 110.0, 110.1, 110.2, 142.2, 161.7, 164.2 ppm. FAB-HRMS Calcd for C$_{21}$H$_{23}$F$_4$NO$_4$Cs: 562.0618. Found: [M+Cs]$^+$ 562.0602.

Synthesis of (3S,4R,5R,6S)-3,6-di-O-(3'-Fluorobenzyl)-N-methyl-3,4,5,6-tetrahydroxyazepane N-oxide (65a) as Illustrated in FIG. 19

Compound 64a (13.3 mg, 0.03 mmol) was suspended in 2 mL of distilled water and 20 mg of 50% hydrogen peroxide was added. The reaction mixture was allowed to stir for 2 days at room temperature. The water was evaporated to give a white powder. The crude product was purified by preparative tlc (500 μm, developed with 15% methanol in dichloromethane, v/v). The product was obtained as a white powder (13.2 mg, yield 95%). R$_f$ 0.16 (methanol:dichloromethane=1:9, v/v). $^1$H NMR (400 MHz, CD$_3$OD) δ3.22 (3H, 8), 3.51–3.76 (7H, m), 3.96 (1H, m), 4.72 (4H, m), 7.00 (2H, m), 7.21 (4H, m), 7.34 (2H, m) ppm. $^{13}$C NMR (CD$_3$OD) δ60.1, 68.9, 70.2, 72.0, 72.5, 75.6, 76.0, 77.1, 79.2, 115.5, 115.7, 115.9, 131.2 ppm. FAB-HRMS Calcd for C$_{21}$H$_{25}$F$_2$NO$_5$Cs: 542.0755. Found: [M+Cs]$^+$ 542.0767.

Synthesis of (3S,4R,5R,6S)-3,6-di-O-(3',5'-difluorobenzyl)-N-methyl-3,4,5,6-tetrahydroxyazepane N-oxide (65b) as Illustrated in FIG. 19

Compound 65b was prepared in a similar way as 65a, except the starting material used was 64b. Compound 65b was isolated as a white powder. Yield 93%. $R_f$ 0.38 (methanol:dichloromethane=2:8, v/v). $^1$H NMR (400 MHz, CD$_3$OD) δ3.28 (3H, s), 3.49–3.75 (7H, m), 3.98 (1H, t, J=7.7 Hz), 4.73 (4H, m), 6.84 (2H, m), 7.05 (4H, m) ppm. $^{13}$C NMR (CD$_3$OD) δ60.4, 68.9, 70.0, 71.4, 71.7, 75.7, 76.3, 77.4, 78.8, 103.3, 103.4, 103.5, 103.7, 103.8, 103.9, 111.2, 111.3, 111.5, 111.6 ppm. FAB-HRMS Calcd for C$_{21}$H$_{23}$F$_4$NO$_5$Cs: 578.0567. Found: [M+Cs]$^+$ 578.0548.

Inhibition Analysis

Inhibition analyses were performed at 37° C. in 0.1 M HEPES buffer, pH=6.8, except for α-fucosidase (assayed at 37° C. in 50 mM sodium acetate buffer, pH 6.0). The amount of enzyme added in each assay was 0.05 units (0.1 units for β-galactosidase and α-fucosidase). For each inhibitor, four inhibitor concentrations, ranging 0–3 times $K_m$, were used to obtain a set of data. p-Nitrophenyl-glycosides were used as substrates and the release of p-nitrophenol was monitored at 400 nm for 2 minutes. Data were collected and fitted to a Michaelis-Menten curve by using the program HyperCleland for enzyme kinetics analysis (Cleland, W. W. *Methods Enzymol.* 1979, 63, 103).

Inhibition Analysis of tetrahydroxyazepanes Against HIV and FIV Proteases

For determination of IC$_{50}$ values for HIV protease, a backbone engineered HIV-1 protease was prepared by total synthesis (Schnolzer et al. *Science* 1992, 256, 221) 450 nM Final concentration of the protease was added to a solution (152 μL final volume) containing tetrahydroxyazepane (inhibitor), 28 μM fluorogenic peptide substrate (Abz-Thr-Ile-Phe-(p-NO$_2$)-Gln-Arg-NH$_2$) (Tith et al. *Int. J. Peptide Protein Res.* 1990, 36, 544; Slee, et al. *J. Am. Chem. Soc.* 1995, 117, 11867) and 1.8% dimethyl sulfoxide in assay buffer: 100 mM MES buffer containing 0.5 mg/mL BSA (bovine serum album) at pH 5.5. A $K_m$ of 37±8 μM was reported for the synthetic HIV protease against the above fluorogenic substrate. The assay concentrations of each inhibitor are listed in FIG. 20. The solution was mixed and incubated over 5 minutes at 37° C. during which time the rate of substrate cleavage was monitored by continuously recording the change in fluorescence of the assay solution. An excitation filter of 325 nm and an emission filter of 420 nm were used. For each inhibitor concentration, three measurements were carried out. These data were converted into μM substrate cleaved per minute, using a predetermined standard calibration curve of change in fluorescence against concentration of substrate cleaved.

The inhibitory effects of compounds 60a, 60b, 64a, 64b, 65a, and 65b on the enzymatic activity of recombinantly derived FIV protease (Slee et al. *J. Am. Chem. Soc.* 1995, 117, 11867) were studied using a fluorogenic assay based on the enzymatic cleavage of a novel peptide based substrate [Arg-Ala-Leu-Thr-Lys(aminobenzyl)-Val-Gln-Phe-Val-Gln-Ser-Lys-Gly-Arg]. Inhibition studies were carried out at a single substrate concentration (20 μM) in a 50 mM sodium citrate/100 mM sodium phosphate buffer (pH 5.3) containing 2% DMSO and 1M sodium chloride. The same wavelengths were used for detections. Under these conditions the fluorogenic substrate displayed a $K_m$ of 14 μM and a $k_{cat}$ of 0.9 s$^{-1}$. IC$_{50}$ values were determined by least squares analysis of Dixon Plots (Dixon, M. *J. Biochem.* 1953, 55, 170).

What is claimed is:

1. A method for producing a tetrahydroxyazepane which comprises the following steps:

step (a): adding 3-azido-2-hydroxypropanaldehyde with dihydroxyacetone phosphate using an aldolase for producing a 6-azido-3,4,5-trihydroxy-2-hexanone-1-phosphate intermediate having an anion represented by the formula:

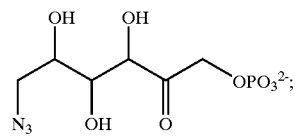

step (b): hydrolyzing the 6-azido-3,4,5-trihydroxy-2-hexanone-1-phosphate intermediate formed in said step (a) with acid phosphatase for producing a polyhydroxy 6-deoxy-6-azido ketose intermediate with the formula:

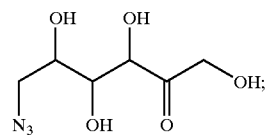

step (c): isomerizing the polyhydroxy 6-deoxy-6-azido ketose intermediate formed in said step (b) with an isomerase for producing a 6-azido-6-deoxyaldose intermediate with the formula:

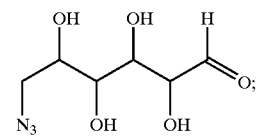

step (d): cyclizing the 6-azido-6-deoxyaldose intermediate formed in said step (c) using reductive amination conditions with hydrogen and a catalyst for producing the tetrahydroxyazepane with the formula:

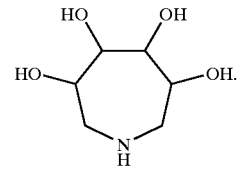

2. The method as described in claim 1 wherein said aldolase is selected from the group consisting of rhamnulose-1-phosphate aldolase, rabbit muscle aldolase, fructose-1,6-diphosphate aldolase and fucose aldolase.

3. The method as described in claim 1 wherein said isomerase is selected from the group consisting of rhamnose isomerase, fucose isomerase, glucose isomerase and galacatose isomerase.

4. The method as described in claim 1 wherein said catalyst is selected from the group consisting of palladium on carbon and platinum on carbon.

5. A method for producing a tetrahydroxyazepane which comprises the following step:

step (a): cyclizing a 6-azido-6-deoxyaldose intermediate with the formula:

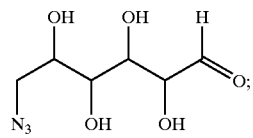

using reductive amination conditions with hydrogen and a catalyst for producing the tetrahydroxyazepane with the formula:

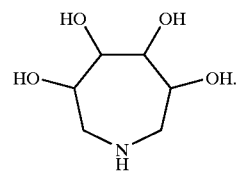

6. The method as described in claim 5 wherein said catalyst is selected from the group consisting of palladium on carbon and platinum on carbon.

7. A compound represented by the following structure:

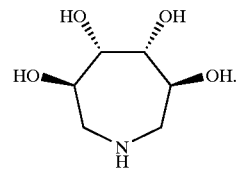

* * * * *